United States Patent [19]

Frost et al.

[11] Patent Number: 5,776,736
[45] Date of Patent: Jul. 7, 1998

[54] DEBLOCKING THE COMMON PATHWAY OF AROMATIC AMINO ACID SYNTHESIS

[75] Inventors: John W. Frost, Okemos, Mich.; Kristi D. Snell, Belmont, Mass.; Karen M. Frost, Okemos, Mich.

[73] Assignee: Purdue Research Foundation, West Lafayette, Ind.

[21] Appl. No.: 257,354

[22] Filed: Jun. 9, 1994

Related U.S. Application Data

[63] Continuation-in-part of Ser. No. 994,194, Dec. 21, 1992, abandoned.

[51] Int. Cl.$^6$ .......................... C12P 13/22; C12N 1/21; C12N 15/70; C07H 21/04
[52] U.S. Cl. ............... 435/108; 435/252.33; 435/320.1; 536/23.2; 536/23.7
[58] Field of Search ............. 435/240.2, 172.3, 435/69.1, 252.3, 252.33, 320.1, 108, 106; 536/23.2, 23.7

[56] References Cited

U.S. PATENT DOCUMENTS

| | | | |
|---|---|---|---|
| 3,970,522 | 7/1976 | Sasajima et al. | 435/105 |
| 4,681,852 | 7/1987 | Tribe | 435/108 |
| 4,753,883 | 6/1988 | Backman et al. | 435/232 |
| 4,908,312 | 3/1990 | Ozaki et al. | 435/108 |
| 4,980,285 | 12/1990 | Sano et al. | 435/108 |
| 5,017,481 | 5/1991 | Matsui et al. | 435/108 |
| 5,168,056 | 12/1992 | Frost | 435/172.3 |
| 5,272,073 | 12/1993 | Frost et al. | 435/155 |
| 5,304,475 | 4/1994 | Kim et al. | 435/108 |
| 5,407,824 | 4/1995 | Katsumata et al. | 435/252.32 |

OTHER PUBLICATIONS

James E. Bailey, Science, vol. 252, 21 Jun. 1991, pp. 1668–1675.
Ogino, Takashi et al., "Biosynthesis of aromatic compounds: $^{13}$C NMR spectroscopy of whole *escherichia coli* cells", Oct., 1982, *Proc. Nat'l Acad. Sci. USA*, vol. 79, pp. 5828–5832.
Herrmann, Klaus M., "The Common Aromatic Biosynthetic Pathway", 1983, *Amino Acids: Biosynthesis and Genetic Regulation*, Addison-Wesley Reading, pp. 301–378.
Frost, John W. et al., "Dehydroquinate Synthase from *Escherichia coli*: Purification, Cloning, and Construction of Overproducers of the Enzyme", 1984, *Biochemistry*, pp. 4470–4475.
Pittard, A.J., "Biosynthesis of the Aromatic Amino Acids", 1987, *Escherichia coli and Salmonella typrimurium*, American Society for Microbiology, Washington, pp. 368–394.
Backman, Keith et al., "Genetic Engineering of Metabolic Pathways Applied to the Production of Phenylalanine", *Annals New York Academy of Sciences*, pp. 16–24 (1988).
Ito, Hisao et al., "Improvement in Microbial Production of L–Tyrosine by Gene Dosage Effect of AroL Gene Encoding Shikimate Kinase", 1990, *Agric. Biol. Chem.*, vol. 54(3), pp. 823–824.
Venkat, K. et al., Abstract "Genetic Manipulation of the Shikimate Pathway to Overproduce Aromatic Amino Acids", 1990, *Food Biotechnology*, vol. 4(1), p. 547.
Draths, K.M. et al., "Genomic Direction of Synthesis During Plasmid–Based Biocatalysis", 1990, *J. Am. Chem. Soc.*, vol. 112, p. 9630.
Draths, K.M. et al., "Synthesis Using Plasmid–Based Biocatalysis: Plasmid Assembly and 3–Deoxy–D–arabino–heptulosonate Production", 1990, *J. Am. Chem. Soc.*, vol. 112, pp. 1657–1659.
Draths, K.M. et al., "Conversion of D–Glucose into Catechol: The Not–So–Common Pathway of Aromatic biosynthesis", 1991, *J. Am. Chem. Soc.*, vol. 113, pp. 9361–9363.
Borman, Stu, "New biosynthetic route to catechol discovered", Jan. 6, 1992, *Science/Technology*, p. 26.

*Primary Examiner*—David Guzo
*Attorney, Agent, or Firm*—Barnes & Thornburg

[57] ABSTRACT

Enhanced efficiency of production of aromatic compounds via the common pathway, as shown in FIG. 1, of a host cell is realized by increasing the expression of enzyme species acting on substrate intermediates in identified rate-limiting reaction steps in the pathway. Prokaryotic cell transformants are described comprising exogenous DNA sequences encoding for the enzymes species, 3-dehydroquinate synthase, shikimate kinase, 5-enolpyruvoyl-shikimate-3-phosphate synthase and chorismate synthase. These transformants can be further transformed with exogenous DNA sequences encoding the enzyme species transketolase and DAHP synthase. In one embodiment of the present invention, one or more of the DNA sequences encoding the enzyme species are incorporated into the genome of the transformant.

14 Claims, 35 Drawing Sheets

Design of Synthetic Cassette.

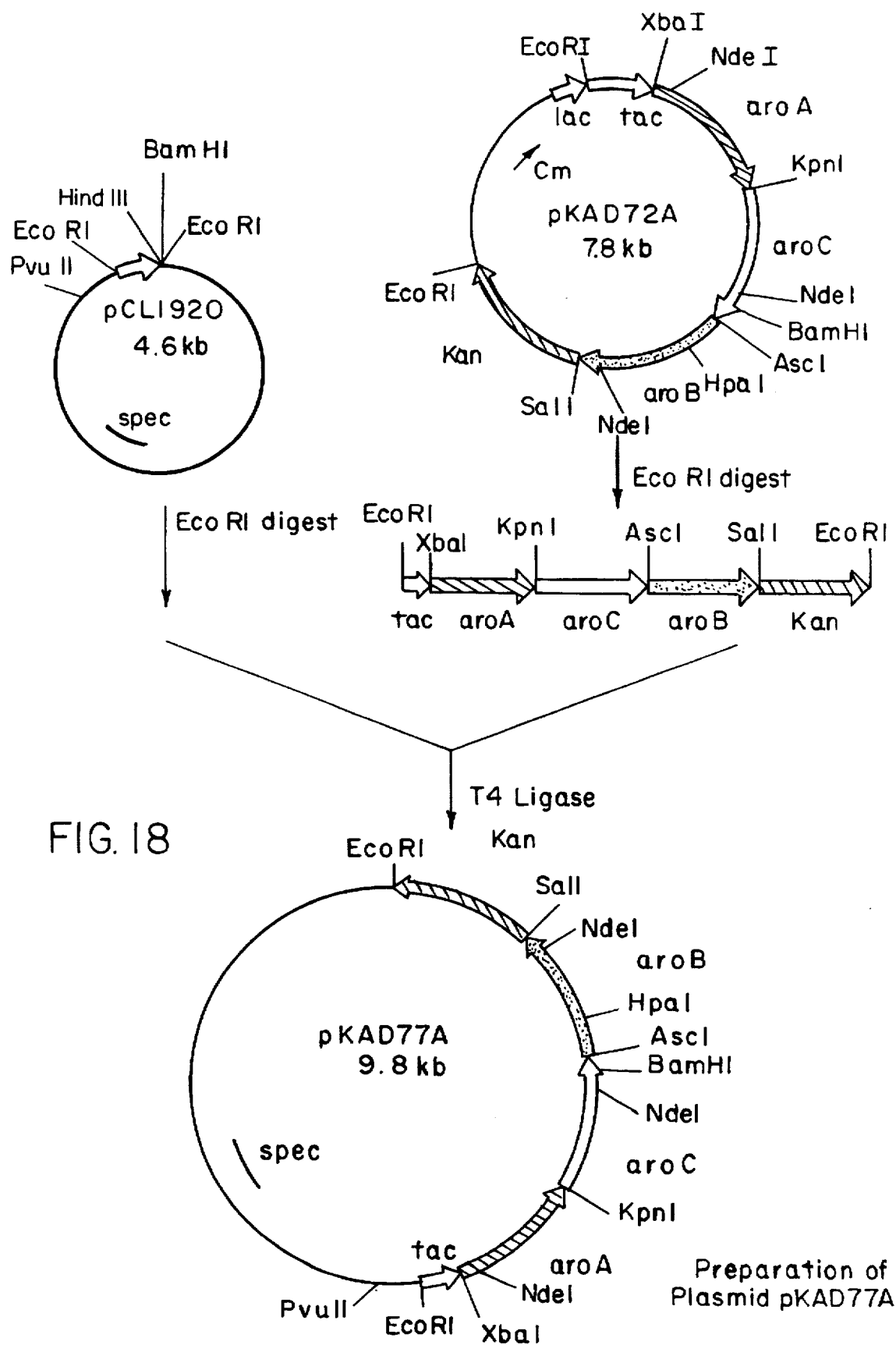
FIG. 18  Preparation of Plasmid pKAD77A $\Omega$ = transcription termination sequence → = promoter Location of Promoters and Transcription Termination Sequences in Cassette Fragments Preparation of Plasmid pKAD69

FIG. 23  Preparation of Plasmid pKAD70

Preparation of Plasmid pKAD68

Preparation of Plasmid pKAD62A

Preparation of Plasmid pKAD73

Preparation of Plasmid pKAD74

Preparation of Plasmids pKAD72A and pKAD72B

Preparation of Plasmid pKAD76A

Preparation of Plasmid pKAD80A

DEBLOCKING THE COMMON PATHWAY OF AROMATIC AMINO ACID SYNTHESIS

CROSS-REFERENCE TO RELATED APPLICATIONS

This application is a continuation-in-part of U.S. patent application Ser. No. 07/994,194, filed Dec. 21, 1992, now abandoned.

FIELD OF THE INVENTION

This invention relates to the enhancement of the efficiency of biosynthetic reactions. More particularly this invention is directed to a method for enhancing the biosynthesis of aromatic compounds in the common pathway in a host cell by genetically engineering the host cell to effectively remove the rate-limiting steps of the pathway.

BACKGROUND AND SUMMARY OF THE INVENTION

The common pathway of aromatic amino acid biosynthesis, otherwise known as the shikimate pathway, produces the aromatic amino acids, phenylalanine, tyrosine, and tryptophan in bacteria and plants. The route to the aromatic amino acids consists of a common pathway that ends in the branch point molecule chorismate which is subsequently converted to phenylalanine, tyrosine and tryptophan by three separate terminal pathways. The aromatic amino acids are essential supplements to the diets of humans and animals who lack the ability to synthesize the compounds. They are also precursors for many interesting and commercially important molecules such as aspartame, a synthetic sweetener, indigo, a common dye, and L-DOPA, a drug used to combat the effects of Parkinson's disease, to name a few.

The success of any biocatalytic route to overproduce the aromatic amino acids or their derivatives from a readily available carbon source such as glucose or other sugars depends on the ability to direct a surge of carbon through the pathway of the host organism. Metabolic blocks encountered in the pathway can effect the subsequent yield and purity of products produced by the biocatalytic conversion.

Earlier approaches for increasing efficiency of production of the common pathway of aromatic biosynthesis have been described in U.S. Pat. No. 5,186,056, issuing Dec. 1, 1992, on U.S. application Ser. No. 07/652,933, filed Feb. 8, 1991, the disclosure of which is expressly incorporated herein by reference. That patent describes a related invention directed to increasing the carbon flow into the pathway by increasing the in vivo catalytic activity of 3-deoxy-D-arabino-heptulosonate-7-phosphate synthase and transketolase. While the aforementioned patent teaches increasing carbon flow into the common pathway, it has been found that increased carbon flow directed into the common pathway is lost if there are one or more pathway enzymes that are not able to catalyze conversion of intermediate substrates to products at rates comparable to the rate at which those substrate intermediates are produced. Thus, there are certain ratelimiting steps in the biosynthetic pathway that work to impede the progress of the reaction steps through the pathway. The present invention removes those impediments.

The analysis of culture supernatants of the *Escherichia coli* strain D2704 (pheA-, tyrA-, ΔtrpE-C) using nuclear magnetic resonance spectroscopy (NMR) has identified 3-dehydroquinate synthase, shikimate kinase, 5-enolpyruvoylshikimate-3-phosphate synthase, and chorismate synthase as rate-limiting enzymes in the common pathway of aromatic amino acid biosynthesis. Transformation of *Escherichia coli* strain D2704 with exogenous DNA sequences encoding the common pathway enzyme species 3-dehydroquinate synthase (aroB), shikimate kinase (aroL), 5-enolpyruvoylshikimate-3-phosphate synthase (aroA), and chorismate synthase (aroC) resulted in a significant increase in end product production.

BRIEF DESCRIPTION OF THE DRAWINGS

FIG. 18 illustrates the construction of plasmid pKAD77A.

DETAILED DESCRIPTION OF THE INVENTION

Figure 1:
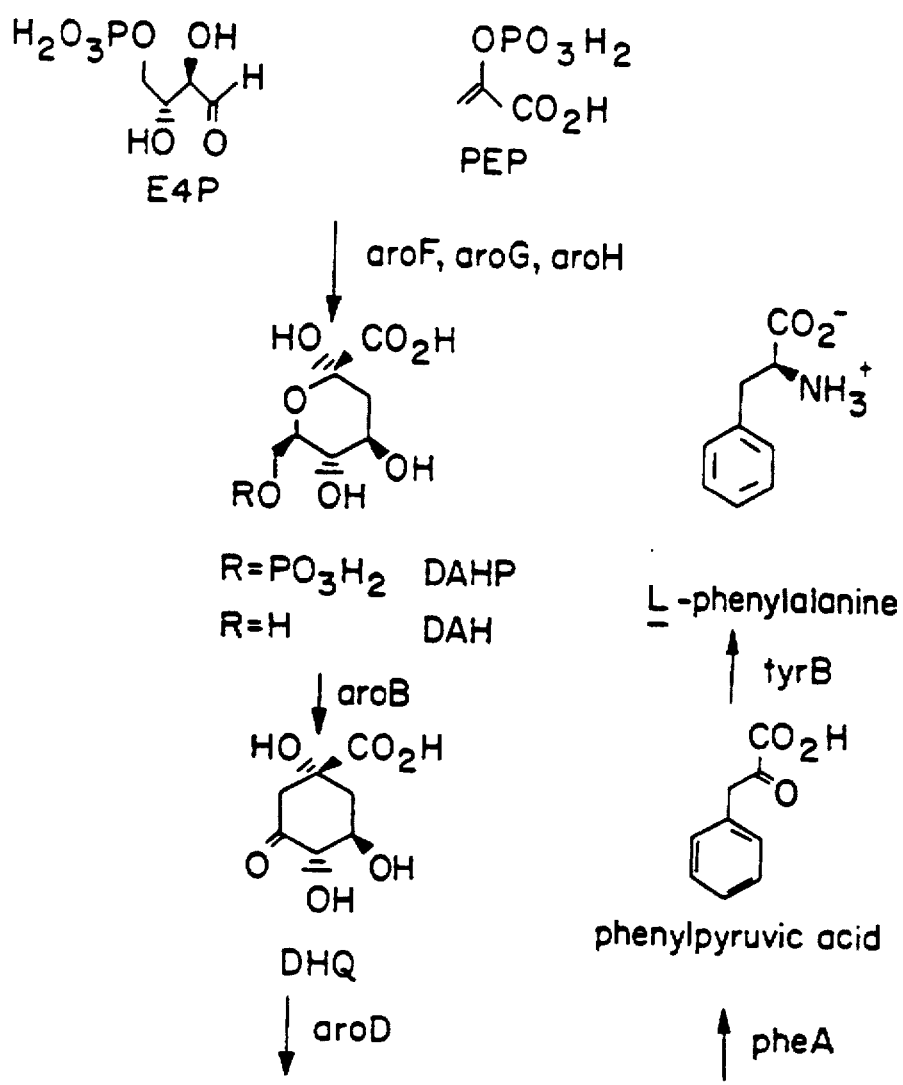
FIG. 1 illustrates the common pathway of aromatic amino acid biosynthesis.

In accordance with this invention there is provided a method for enhancing the production of an aromatic compound in a host cell via the common pathway of aromatic amino acid biosynthesis (the common pathway) endogenous to the host cell. In that pathway a metabolizable carbon source is converted to intermediate aromatic compounds in a multiple step reaction sequence characterized by enzyme species acting on intermediate substrates.

It has been reported that enhancing the expression of all the common pathway enzymes decreases the production of common pathway end products. However, applicants have discovered that enhancing the expression of a subset of pathway enzymes results in significant enhanced production of pathway end products. More specifically, applicants have identified the rate-limiting steps in the pathway, and have discovered that enhancing the expression of the enzyme species catalyzing the rate limiting steps (3-dehydroquinate synthase, shikimate kinase, 5-enolpyruvoylshikimate-3- phosphate synthase (EPSP synthase), and chorismate synthase) significantly enhances the production of pathway end products.

In one embodiment the biosynthesis of aromatic compounds is enhanced by transforming a host cell with recombinant DNA comprising exogenous DNA sequences encoding common pathway enzyme species, said enzyme species consisting essentially of the enzymes 3-dehydroquinate synthase, shikimate kinase, 5-enolpyruvoylshikimate-3-phosphate synthase, and chorismate synthase, and culturing the transformed cell in media containing a metabolizable carbon source. Alternatively, enhanced expression of the enzyme species involved in the rate-limiting steps can be achieved by genetically engineering the host cell to overexpress endogenous genes for such enzyme species, either by modification of endogenous control sequences or by affecting derepression of existing expression control sequences utilizing art accepted methods.

Regardless of the exact mechanism utilized for enhancing expression of the rate-limiting enzyme species, it is contemplated that such will typically be effected or mediated by the transfer of recombinant genetic elements into the host cell. Genetic elements as herein defined include nucleic acids (generally DNA or RNA) having expressible coding sequences for products such as proteins, specifically enzymes, apoproteins or antisense RNA, which express or regulate expression of rate-limiting enzymes in the common pathway. The expressed proteins can function as enzymes, repress or derepress enzyme activity, or control expression of enzymes. Recombinant DNA encoding these expressible sequences can be either chromosomal (integrated into the host cell chromosome by, for example, homologous recombination) or extrachromosomal (for example, carried by plasmids, cosmids, and other vectors capable of effecting the targeted transformation). It is understood that the recombinant DNA utilized for transforming the host cell in accordance with this invention can include, in addition to structural genes, expression control sequences including promoters, repressors, and enhancers that act to control expression or derepression of coding sequences for proteins, apoproteins or antisense RNA. For example, such control sequences can be inserted into wild type host cells to promote overexpression of selected enzymes already encoded in the host cell genome, or alternatively, they can be used to control synthesis of extrachromosomally encoded enzymes.

The recombinant DNA can be introduced into the host cell by plasmids, cosmids, phages, yeast artificial chromosomes or other vectors that mediate transfer of genetic elements into a host cell. These vectors can include an origin of replication along with cis-acting control elements that control replication of the vector and the genetic elements carried by the vector. Selectable markers can be present on the vector to aid in the identification of host cells into which genetic elements have been introduced. Exemplary of such selectable markers are genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention have been inserted. Plasmid borne introduction of the genetic element into host cells involves an initial cleaving of a plasmid vector with a restriction enzyme, followed by ligation of the plasmid and genetic elements encoding for the targeted enzyme species in accordance with the invention. Upon recircularization of the ligated recombinant plasmid, infection (e.g., packaging in phage lambda) or other mechanism for plasmid transfer (eg. electroporation, microinjection, etc.) is utilized to transfer the plasmid into the host cell. Plasmids suitable for insertion of genetic elements into the host cell include but are not limited to pBR322 and its derivatives such as pAT153, pXf3, pBR325, and pBR327, pUC vectors and their derivatives, pACYC and its derivatives, pSC101 and its derivatives, and ColE1.

Suitable host cells for use in the present invention are members of those genera capable of being utilized for industrial biosynthetic production of desired aromatic compounds. This includes any of the nonphotosynthetic eubacteria cells including prokaryotes belonging to the genera Escherichia, Corynebacterium, Brevibacterium, Arthrobacter, Bacillus, Pseudomonas, Streptomyces, Staphylococcus, or Serratia. More preferably prokaryotic cells are selected from the genera Escherichia, Corynebacterium, Brevibacterium, most preferably the genera Escherichia. Eukaryotic host cells can also be utilized, with yeasts of the genus Saccharomyces or Schizosaccharomyces being preferred.

More specifically, prokaryotic host cells are derived from, but not limited to, species that include *Escherichia coli, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomryces coelicolor Streptomyces griseus, Streptomyces kasugensis, Streptomyces lavendulae, Streptomyces lipmanii, Streptomyces lividans, Staphylococcus epidermis, Staphylococcus saprophyticus,* or *Serratia marcescens.* Preferred eukaryotic host cells include *Saccharomyces cerevisiae* or *Saccharomyces carlsbergensis.*

For industrial production of primary metabolites derived from chorismate (such as aromatic amino acids), deregulated mutant strains of the above recited species that lack feedback inhibition of one or more enzymes in the metabolic biosynthetic pathway are preferred. Such strains can be created by random or directed mutagenesis, or are commercially available. Examples of *E. coli* strains having DAHP synthase, prephenate dehydratase, or chorismate mutase feedback inhibition removed are described in U.S. Pat. No. 4,681,852 to Tribe and U.S. Pat. No. 4,753,883 to Backman et al., the disclosures of which are incorporated herein by reference.

Shikimate kinase is one common pathway enzyme whose in vivo catalytic activity can be increased by mutation of a genomic locus. The aroL sequence encoding shikimate kinase is a part of the aroL aroM operon that is controlled by the tyrR regulon and is transcriptionally repressed in the presence of the TyrR repressor protein and either tyrosine or tryptophan. Transcriptional repression can lead to a 6.9 fold reduction in shikimate kinase activity when cells are grown in the presence of both tyrosine and tryptophan. Applicants have constructed tyrR mutants of *E. coli* strain D2704, which do not produce the TryR repressor protein. Three tyrR mutants, KAD26B, KAD27C, and KAD29B, were isolated. Applicants use these mutant cell lines as one method of enhancing the expression of shikimate kinase. Preferably tyrR− strains KAD27C and KAD29B are utilized, and most preferably KAD29B is used as the tyrR− host cell which is further manipulated to eliminating the remaining rate limiting steps of the common pathway.

Although a tyrR mutation does increase levels of carbon flow through the common pathway by enhancing the expression of shikimate kinase, the effect of the tyrR mutation on other aspects of the cell's metabolic processes must be evaluated. In addition to the aroL aroM operon, eight other transcriptional units involved in either aromatic amino acid biosynthesis or transport are controlled by the tyrR regulon. The aroF tyrA transcriptional unit, encoding the tyrosine-sensitive isozyme of DAHP synthase and the bifunctional enzyme chorismate mutase-prephenate dehydrogenase, and aroG, encoding the phenylalanine sensitive isozyme of DAHP synthase, are transcriptionally repressed in the presence of tyrosine and phenylalanine, respectively. Transcription of the locus encoding the third isozyme of DAHP synthase, aroH, has recently been shown to be under the control of the tyrR regulon. The transcriptional unit mtr, encoding an enzyme involved in tryptophan specific transport, is regulated by induction mediated by the TyrR protein whereas tyrP, encoding an enzyme involved in tyrosine specific transport, is regulated by both repression and induction in the presence of tyrosine and phenylalanine, respectively. In addition, the tyrR regulon regulates the transcription of tyrB, which encodes the aromatic amino transferase, aroP, encoding an enzyme involved in general aromatic transport, and tyrR, encoding the TyrR repressor protein. An additional concern arises from reports that the tyrosine operon, aroF tyrA, is unstable on multi-copy plasmids in tyrR mutants. Plasmids containing the entire aroF tyrA operon, when transformed into a tyrR mutant, are modified through insertion and deletion mutations such that the level of expression of the operon is decreased. Instability of multicopy plasmids containing aroF is of concern given that amplified expression of DAHP synthase, encoded by this locus, is essential to increasing the carbon flow directed into the common pathway.

In preferred embodiments of the present invention, the enhanced expression of the rate-limiting enzyme species in the host cell is achieved by transformation of the host cell with a plasmid vector comprising DNA encoding for the enzyme species 3-dehydroquinate synthase, shikimate kinase, 5-enolpyruvoylshikimate-3-phosphate synthase (EPSP synthase) and chorismate synthase. In a preferred embodiment of the present invention a prokaryotic cell is transformed with recombinant DNA to produce a prokaryotic cell transformant characterized by the expression of exogenous structural genes encoding the enzyme species transketolase (tkt), 3-deoxy-D-arabino-heptulosonate-7-phosphate synthase (DAHP synthase), 3-dehydroquinate synthase (DHQ synthase), shikimate kinase, 5-enolpyruvoylshikimate-3-phosphate synthase, and chorismate synthase. Typically the exogenous structural genes are introduced into the host cell as part of one or more recombinant plasmid vectors comprising the DNA encoding for the enzyme species.

Other embodiments of the present invention include cell transformants prepared in accordance with this invention and a method utilizing such cell transformants to produce an aromatic compound biocatalytically from a carbon source. The method comprises the step of culturing a prokaryote cell transformant in media containing an assimilable source of carbon, said cell transformant comprising exogenous DNA sequences encoding common pathway enzyme species, said enzyme species consisting essentially of the enzymes 3-dehydroquinate synthase, shikimate kinase, 5-enolpyruvoylshikimate-3-phosphate synthase and chorismate synthase. The cell transformant is cultured under conditions conducive to the assimilation of the carbon source, wherein the carbon source is taken up by the cell and utilized in the common pathway. Thus applicants' invention is an improvement of their earlier work described in U.S. Pat. No. 5,186,056 which discloses increasing carbon flow into the common pathway by overexpressing the enzymes transketolase and 3-deoxy-D-arabino-heptulosonate-7-phosphate synthase. As disclosed in the present application, the increased carbon flow directed into the common pathway by the overexpression of transketolase and DAHP synthase is lost unless the rate-limiting steps of the pathway are removed. Applicants' invention is directed to the identification and elimination of these rate-limiting steps by enhancing the expression of common pathway enzymes consisting essentially of the enzymes 3-dehydroquinate synthase, shikimate kinase, 5-enolpyruvoylshikimate-3-phosphate synthase and chorismate synthase.

Other embodiments of the present invention include plasmid constructs comprising structural genes encoding the rate-limiting enzymes of the common aromatic biosynthetic pathway. For example, one preferred construction comprises structural genes for 3-dehydroquinate synthase, EPSP synthase, and chorismate synthase. Most preferably the plasmid construct comprises structural genes for common pathway enzyme species, said enzyme species restricted to the rate-limiting enzymes 3-dehydroquinate synthase, shikimate kinase, 5-enolpyruvoylshikimate-3-phosphate synthase and chorismate synthase. A prokaryote cell transformed with such plasmid constructs is still another contemplated embodiment of the present invention.

As mentioned above, there have been earlier efforts to enhance the biosynthetic production of compounds derived from the common pathway in a host cell by increasing the expression of proteins catalyzing reactions in that pathway. The present invention provides for significant improvement in the efficiency of production of aromatic compounds in host cells via the common pathway. While earlier reports have taught that carbon flow can be increased into the upper end (the initial reaction sequences) of the pathway by enhancing the concentrations of transketolase alone or in combination with other enzymes in the common pathway, for example, DAHP synthase, DHQ synthase and even shikimate kinase, these references failed to teach or suggest the identification and removal of all the rate limiting steps of the common pathway. Applicants have accomplished the removal of the rate limiting steps, and thus have increased the efficiency of carbon flow through the entire pathway, by transforming the host cell with exogenous DNA sequences encoding the rate-limiting enzyme species 3-dehydroquinate synthase (DHQ synthase), shikimate kinase, 5-enolpyruvoylshikimate-3-phosphate synthase, and chorismate synthase to increase expression of those enzymes in the host cell.

Thus the present invention can be viewed as an improvement on earlier efforts to increase the biosynthetic production of compounds derived from the common pathway, the improvement comprising the steps of (1) identifying the rate-limiting reaction steps in said pathway, and (2) increasing expression of those proteins catalyzing the identified rate-limiting steps in the pathway resulting in the removal of the rate-limiting steps. Again, the increased expression is preferably achieved in accordance with this invention by transforming the host cell to express exogenous genes encoding for said protein catalyst (enzyme) to increase concentration of the proteins in the host cell. One preferred prokaryotic cell transformant is characterized by the enhanced expression of structural genes 3-dehydroquinate synthase, shikimate kinase, 5-enolpyruvoylshikimate-3-phosphate synthase and chorismate synthase, wherein the cell comprises exogenous DNA encoding at least one of the enzyme species. The enhanced production of common pathway aromatic compounds has been shown particularly where the host cell is a strain of E. coli transformed to express exogenous structural genes comprising the genes for 3-dehydroquinate synthase, shikimate kinase, EPSP synthase and chorismate synthase. (See Table 1). In preferred embodiments the E. coli transformant further comprises exogenous DNA sequences encoding the enzyme species transketolase and DAHP synthase.

D2704, an *Escherichia coli* strain that is pheA-, tyrA- and ΔtrpE-C should theoretically be able to produce chorismic acid because the terminal pathways leading to phenylalanine, tyrosine, and tryptophan are respectively blocked (FIG. 1). Using this strain, deblocking of the common pathway of aromatic amino acid biosynthesis in *E. coli* when an increased surge of carbon was committed to the pathway was planned with the increased accumulation of chorismate as an indicator of successful blocking. Growth of D2704 cells in rich media followed by resuspension in minimal salts accumulation media gave little or no accumulation of chorismate but yielded significant levels of phenylalanine. The production of phenylalanine can be explained by the non-enzymatic Claisen rearrangement of chorismic acid to prephenic acid followed by dehydration to produce phenylpyruvic acid. Although the enzyme chorismate mutase accelerates the conversion of chorismate to prephenate by $2 \times 10^6$ at 37° C., the reaction can occur in the absence of the enzyme. Prephenic acid has been reported to yield phenylpyruvate non-enzymatically under mildly acidic conditions such as those produced during normal culturing of cells. With the production of phenylpyruvic acid, the microbe should be able to synthesize phenylalanine using the intact amino transferase encoded by tyrB. However significant amounts of phenyllactate were observed in some of the culture supernatants.

The aromatic amino transferase encoded by tyrB transaminates the aromatic keto acid using glutamate as the nitrogen donor and pyridoxal phosphate as a coenzyme. [Mavrides, C. In *Methods in Enzymology*; Academic: San Diego, 1987, 142, pp. 253–267.] The production of phenyllactic acid could be due to insufficient supplies of glutamate in the cell to completely transaminate all of the phenylpyruvic acid. Reduction of phenylpyruvic acid to phenyllactate might occur to regenerate a supply of NAD$^+$ within the cell. An analogous reduction of pyruvate to lactic acid catalyzed by the enzyme lactate dehydrogenase [Holbrook, J. J.; Liljas, A.; Steindel, S. S.; Rossmann, M. G. In *The Enzymes*; Boyer, P. D., Ed.; Academic Press: New York, 1975; Vol. 11, Chap. 4] is known to occur under anaerobic conditions to regenerate a supply of NAD$^+$ for the continued functioning of glycolysis.

The activity of the aromatic amino transferase could also be limited by the presence of the pheA mutation in D2704. It has been shown that the bifunctional enzyme chorismate mutase-prephenate dehydratase encoded by pheA interacts with the aromatic amino transferase in the presence of phenylpyruvate to form a complex in *E. coli* [Powell, J. T.; Morrison, J. F.; *Biochem. Biophys. Acta*, 1979, 568, 467–474]. Since D2704 is pheA-, it should be unable to produce the chorismate mutase-prephenate dehydratase enzyme necessary for complex formation. Although the role of the enzyme-enzyme interaction has not been determined, the possibility exists that the inability to form the complex could affect aminotransferase activity resulting in the buildup of phenylpyruvic acid within the cell. Although the above theories are plausible, the reason for phenyllactate accumulation has yet to be determined experimentally. However it is safe to assume that phenyllactate accumulation represents deblocked glucose equivalents from the common pathway. Therefore the successful removal of metabolic blocks from the common pathway of aromatic amino acid biosynthesis was measured by the combined total accumulation of phenylalanine and phenyllactic acid in the following study. Accumulation of common pathway intermediates in the culture supernatant was used to identify enzymes that were rate-limiting steps in the flow of carbon down the common pathway using the notion that the accumulated intermediate was the substrate of a rate-limiting enzyme.

Five milliliter starter cultures of each strain were grown in LB media containing the appropriate drugs for ten hours. The starter cultures were used to inoculate one liter cultures of LB in four liter erlenmeyer flasks with isopropyl β-D-thiogalactopyranoside (IPTG) (0.2 mM), chloramphenicol (20 mg/L), and ampicillin (50 mg/L) added where needed. The one liter cultures were grown for 12 hours at 37° C. with agitation (250 RPM). Cells were harvested (3,000 g; 5 minutes; 4° C.) and washed three times with M9 salts [M9 salts contain (per liter): 6 g Na$_2$HPO$_4$, 3 g KH$_2$PO$_4$, 0.5 g NaCl, 1 g NH$_4$Cl] (300 mls wash for each sample). Cell pellets were resuspended in one liter of M9 accumulation media in a four liter erlenmeyer flask containing glucose (10 g), MgSO$_4$ (1 mM), and thiamine (30 mg) with the addition of chloramphenicol, ampicillin and IPTG where needed. Cells were incubated for an additional 48 hours in the accumulation media at 37° C. with agitation (250 RPM). Aliquots (25 ml) were removed at 24 and 48 hour intervals and centrifuged (6,000 g; 5 min; 4° C.). Ten milliliters of isolated supernatant was collected from each sample and the water was removed in vacuo. Samples were exchanged two times with D$_2$O and analyzed by $^1$H NMR. The sodium salt of 3-(trimethylsilyl) propionic-2,2,3,3-d$_4$ acid was used as the internal standard to quantify intermediates and end products produced in the accumulation. All cultures were grown in triplicate so that mean values of accumulated molecules as well as their standard deviations could be obtained.

Figures 1, 2:
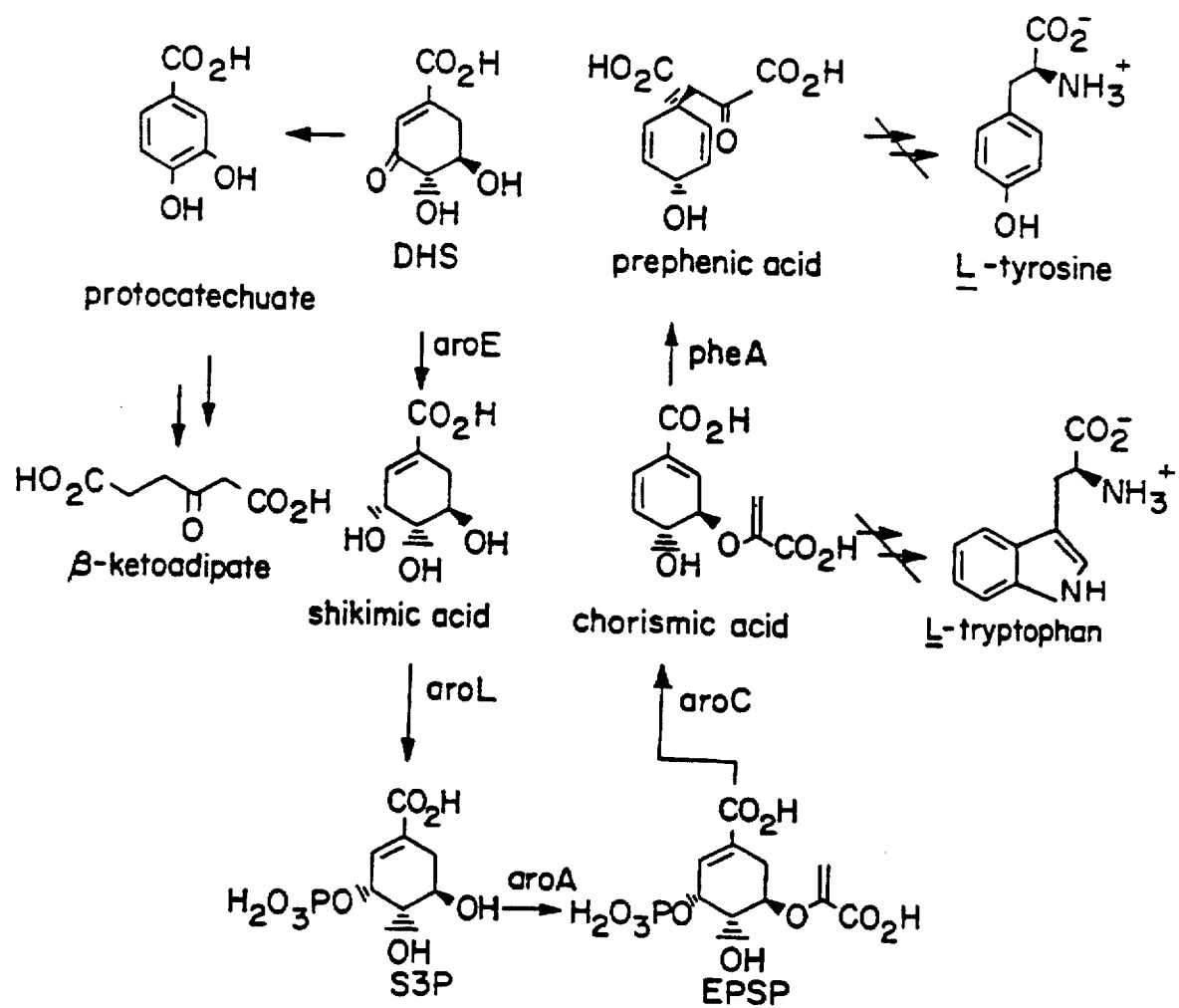
FIG. 2 presents plasmid maps of pKD130A and pKD136.
Figure 2:
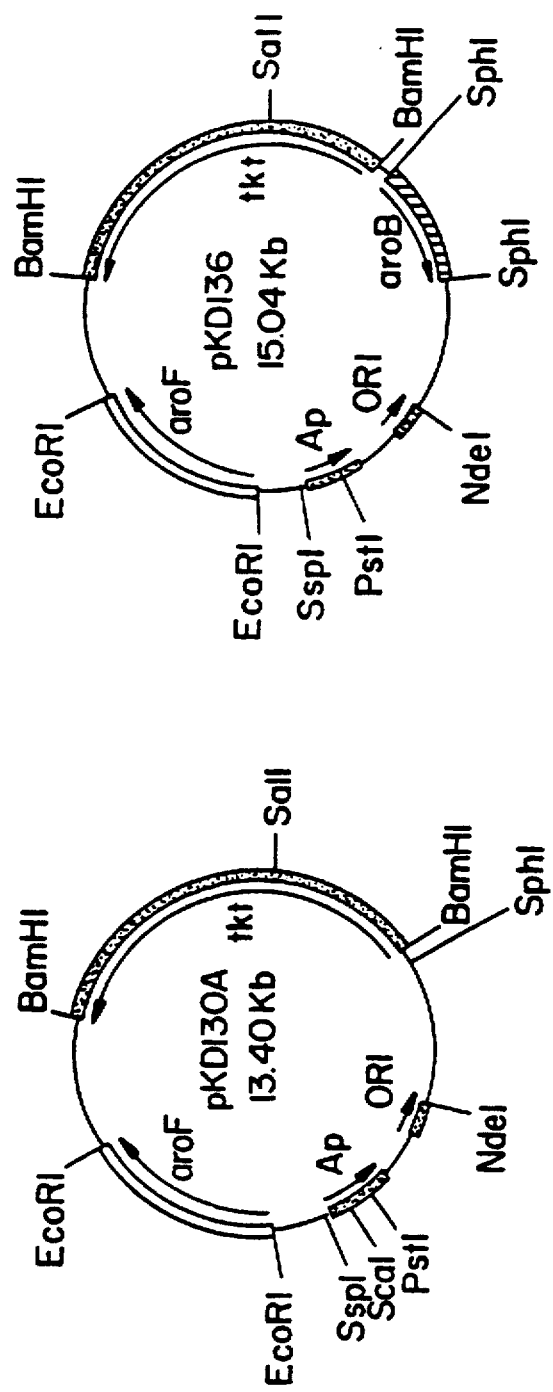
Figure 3A:
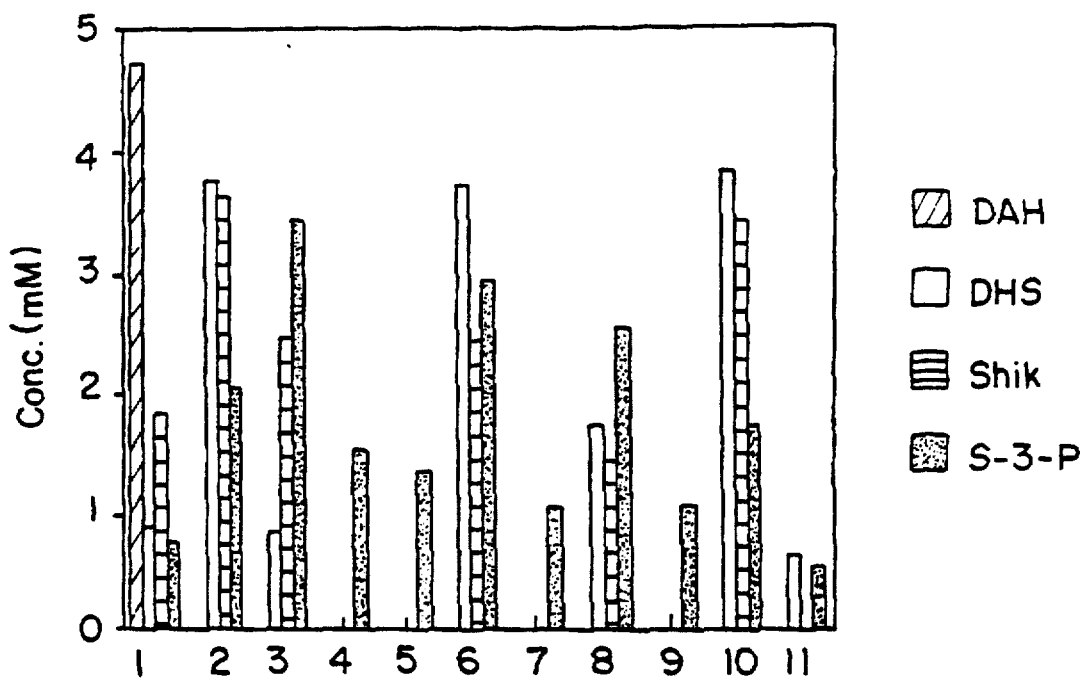
FIGS. 3a and 3b are bar graphs depicting the concentration of common pathway intermediates of D2704 strains of *E. coli* and the average phenylalanine and phenyllactic acid concentrations for those strains.
Figure 3B:
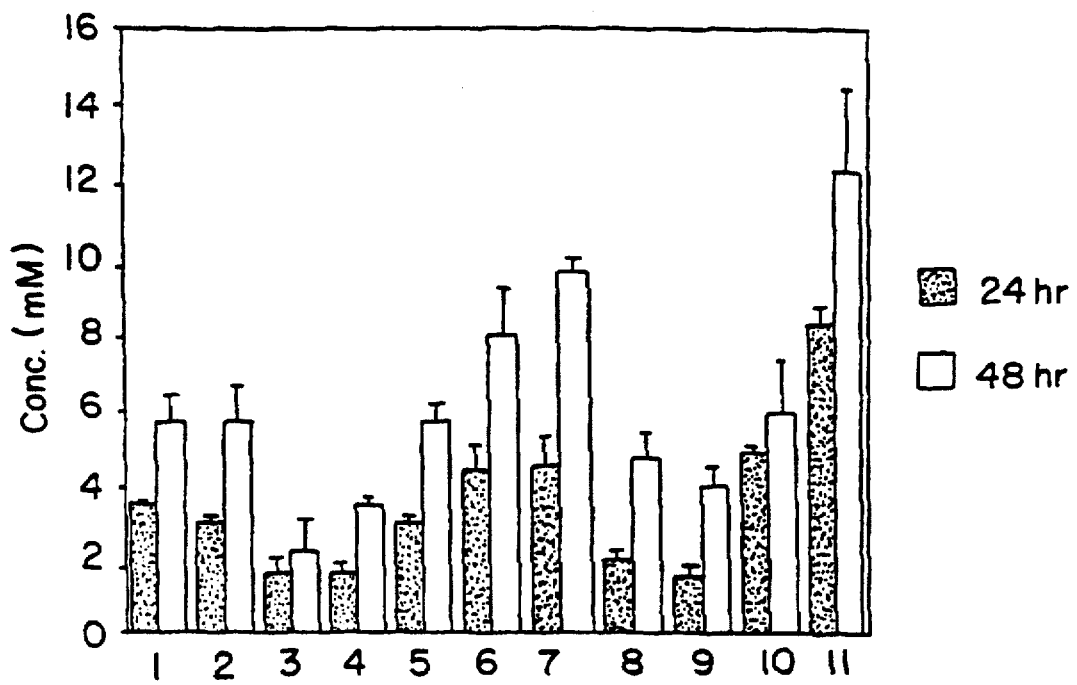

To create a surge of carbon through the common pathway of aromatic amino acid biosynthesis, a plasmid containing transketolase, tkt, and the tyrosine sensitive isozyme of 3-deoxy-D-arabino-heptulosonate-7-phosphate synthase (DAHP synthase), aroF, was employed. Transketolase has been shown to increase the levels of erythrose 4-phosphate available to the cell, for use in producing aromatic amino acids while DAHP synthase is the first irreversible step of the pathway. The tkt, aroF plasmid pKD130A (FIG. 2), a pBR325 derivative with the ampicillin resistance gene intact and a pMB1 origin of replication, accumulated the common pathway intermediates 3-deoxy-D-arabino-heptulosonate-7-phosphate (DAHP), 3-dehydroshikimate (DHS), shikimate and shikimate-3-phosphate with a total phenylalanine and phenyllactate accumulation of 5.6±0.7 mM upon introduction into D2704 (FIG. 3). FIG. 3 represents the data in the form of two bar graphs: FIG. 3A representing the common pathway intermediate accumulated in D2704 strains after 24 hours growth in minimal media; FIG. 3B represents the total accumulation of phenylalanine and phenyllactate after 24 and 48 hours of growth in minimal media. For both FIG. 3A and 3B strains studied include: 1) D2704/pKD130A; 2) D2704/pKD136; 3) D2704/pKD136/pKD28; 4) D2704/ pKD136/pKAD34; 5) D2704/pKD136/pKAD31; 6) D2704/pKD136/pKAD38; 7) D2704/pKD136/pKAD43; 8) D2704/pKD136/pKAD39; 9) D2704/pKD136/pKAD51; 10) D2704/pKD136/pKAD44; 11) D2704/pKD136/pKAD50.

After incubation for 48 hours, $^1$H NMR resonances for DAHP are found at δ 1.79 (dd, 13, 13 Hz, 1 H), δ 2.20 (dd, 13, 5 Hz, 1 H), δ 3.46 (dd, 9, 9 Hz, 1 H) and δ 3.83 (m, 2 H). The presence of shikimate in the culture media is shown by resonances at δ 4.41 (dd, 4, 4 Hz, 1 H) and δ 6.47 (m, 1 H). A resonance for shikimate-phosphate lies at δ 6.47 (m, 1 H). Resonances for phenylalanine are found at δ 3.14 (dd, 14, 8 Hz, 1 H), δ 3.29 (dd, 14, 5 Hz, 1 H) and δ 7.30–7.49 (m, 5 H). Observable resonances for phenyllactic acid are found at δ 4.27 (dd, 8, 4 Hz, 1 H) and δ 7.30–7.49 (m, 5 H). DHS disappeared from the accumulation media between 24 and 48 hours.

The accumulation of DAHP, DHS, shikimate, and shikimate-3-phosphate in the culture supernatant lead to the assignment of 3-dehydroquinate synthase (DHQ synthase), shikimate dehydrogenase, shikimate kinase, and 5-enolpyruvoylshikimate-3-phosphate synthase (EPSP synthase) respectively as rate-limiting enzymes. Although DHQ synthase and shikimate dehydrogenase had been previously identified to be rate-limiting steps in the common pathway, [Draths, K. M.; Frost, J. W.; *J. Am. Chem. Soc.* 1990, 112, 9360–9632; Draths, K. M., Ph.D. Dissertation, Stanford University, June 1991] the identification of shikimate kinase and EPSP synthase as rate-limiting steps has not been reported in the literature.

To remove the accumulation of DAHP in the culture supernatant, a tkt, aroF, aroB plasmid pKD136 (FIG. 2) was introduced into D2704. Using pKD136, DAHP was successfully removed from the culture supernatant resulting in an increased accumulation of DHS, shikimate, and shikimate-3-phosphate but no increase in phenylalanine and phenyllactate (FIG. 3). Thus even though a rate-determining step had been removed from the pathway, no increased accumulation of end product was observed.

Figure 4:
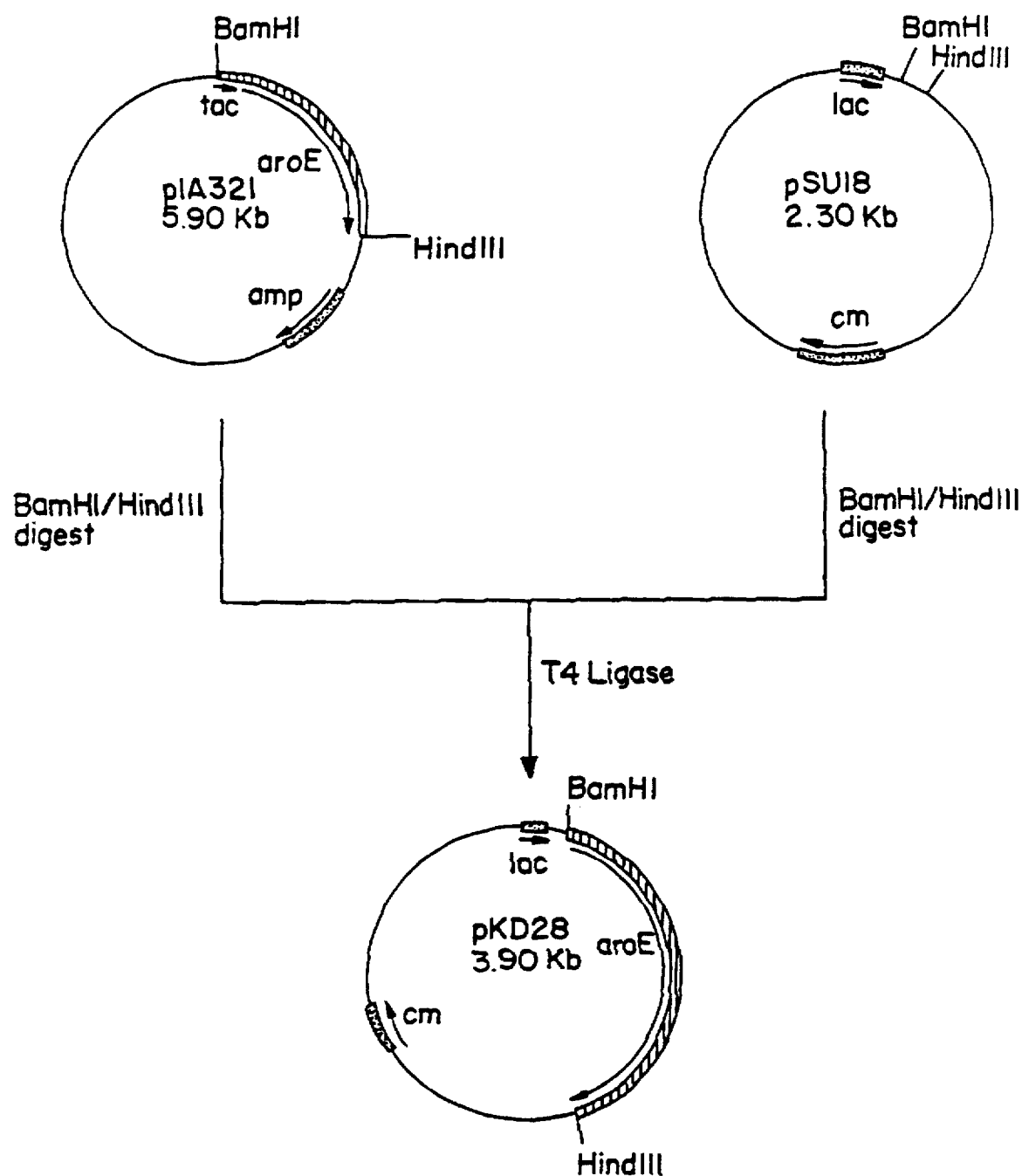
FIG. 4 illustrates the construction of plasmid pKD28 from plasmids pIA321 and pSU18.

The lack of convenient unique restriction sites for the insertion of aroE into pKD136 resulted in the use of a two plasmid system for the rest of the deblocking experiments. The system consisted of pKD136 and the pSU2718/pSU2719 [Martinez, E.; Bartolome, B.; de la Cruz, F. *Gene*, 1988, 68, 159–162] derived plasmids pSU18 and pSU19, possessing chloramphenicol resistance, a lac promoter, and a p15A origin of replication, into which the remaining deblocking genes were inserted. A pSU18 based aroE plasmid, pKD28, [Draths, K. M., Ph.D. Dissertation, Stanford University, June 1991] was created by isolation of a 1.6 kb fragment containing a tac promoter and the aroE gene from pIA321 [Anton, I. A.; Coggins, J. R. *Biochem. J.*, 1988, 249, 319–326] followed by ligation into pSU18 as shown in FIG. 4. D2704/pKD136/pKD28 while reducing the level of DHS accumulation did not completely remove the intermediate from the culture supernatant. Shikimate and shikimate-3-phosphate were still present in the culture broth. The total production of phenylalanine and phenyllactate was reduced to 2.1±0.9 mM after 48 hours of growth (FIG. 3) implying that the increased carbon flow from deblocking at aroE did not result in the additional accumulation of end products.

Figure 5:
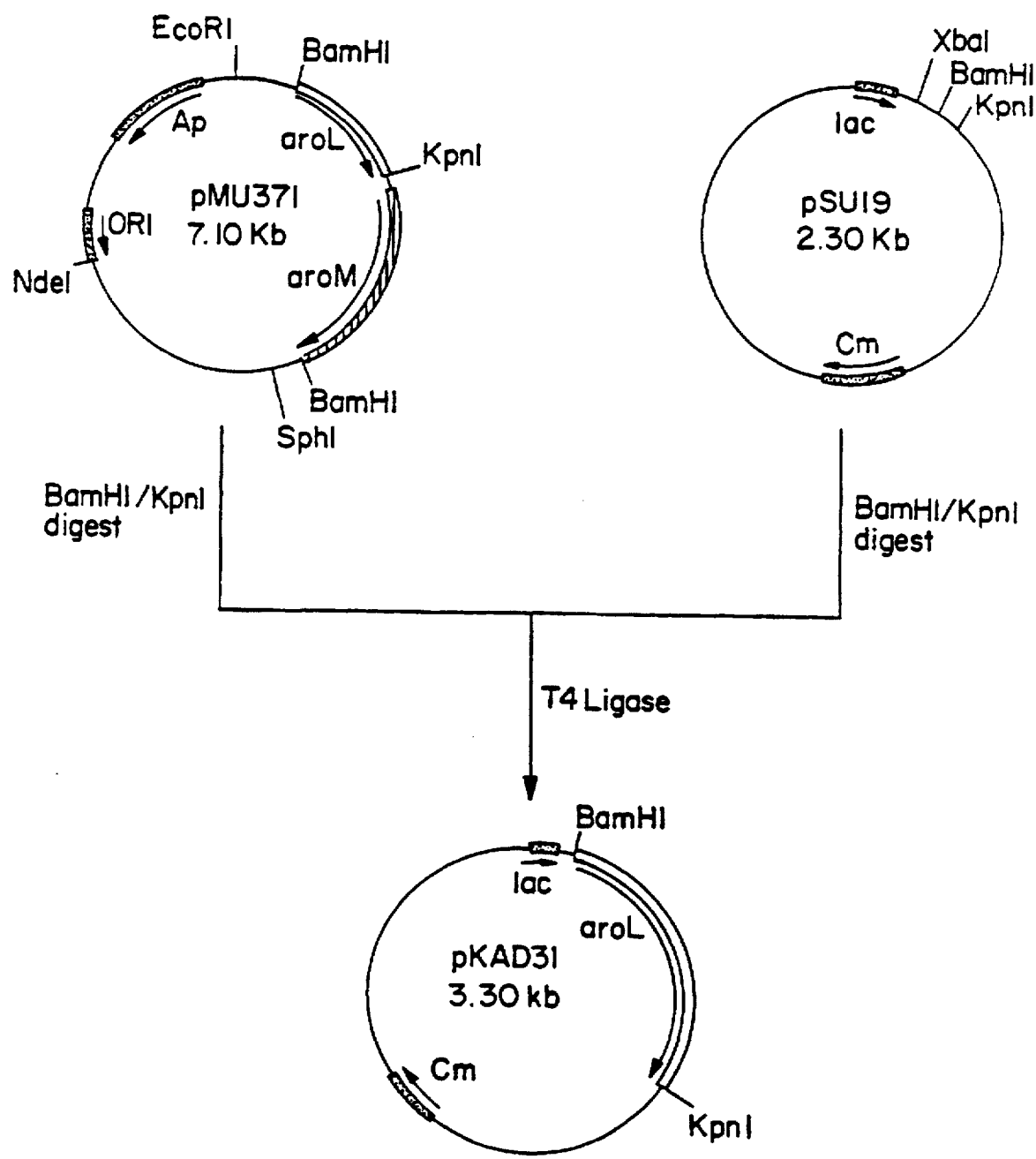
FIG. 5 is similar to FIG. 4 showing construction of plasmid pKAD31.
Figure 6A:
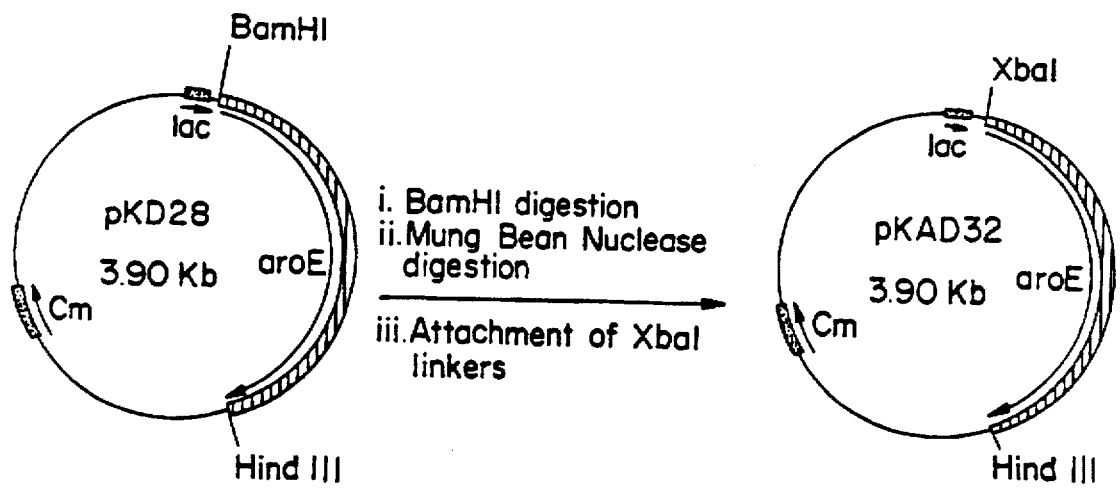
FIGS. 6a and 6b illustrate the preparation of aroEaroL plasmid pKAD34.
Figure 6B:
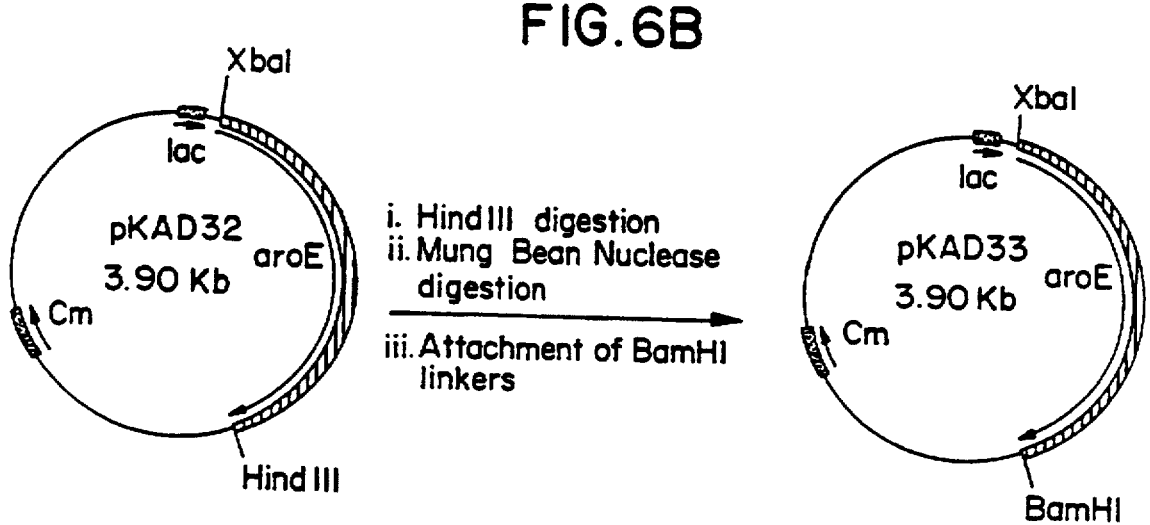
Figure 6C:
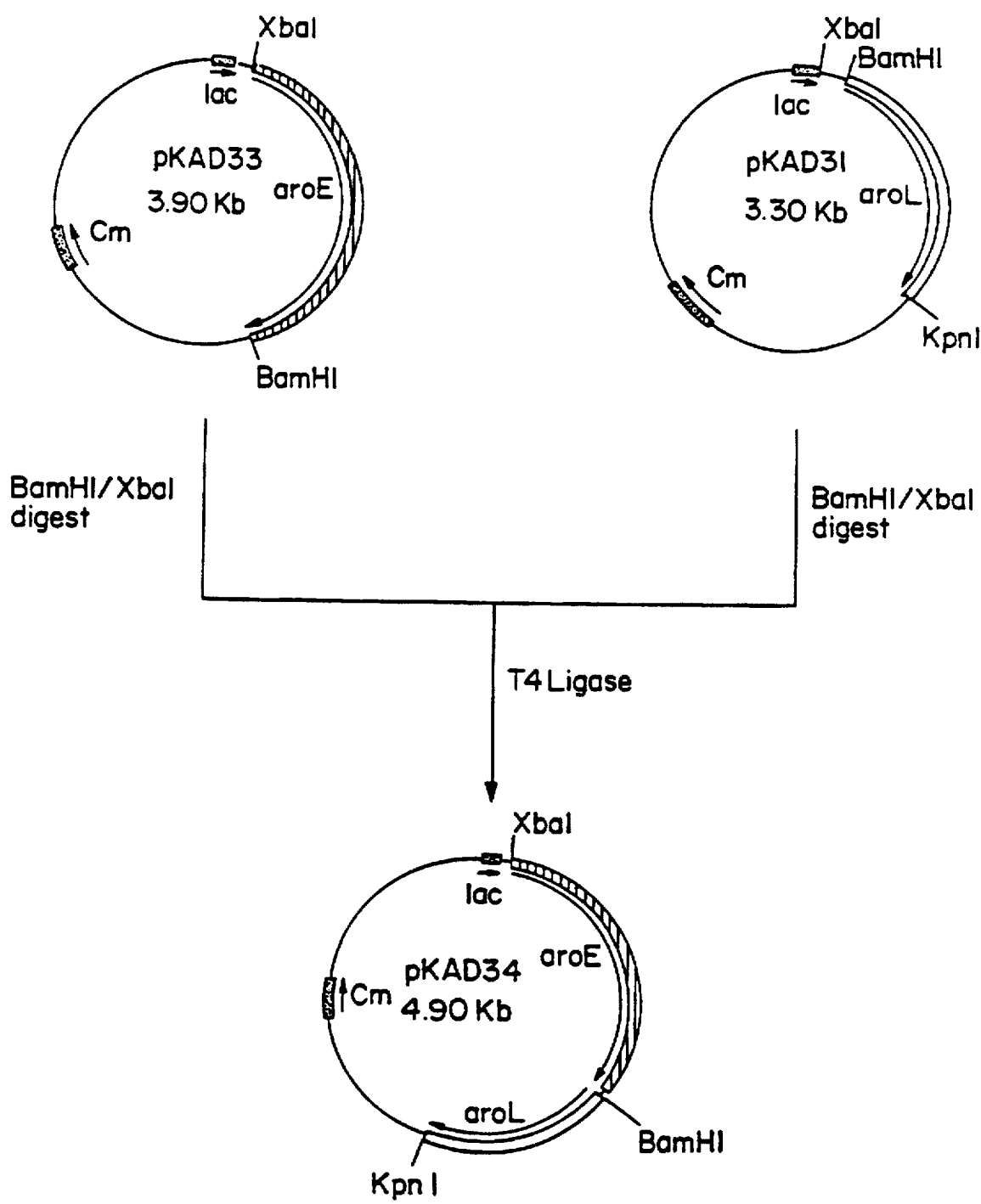

To remove the rate-limiting characteristics of shikimate kinase, both aroL and aroEaroL plasmids were constructed. aroL is located in a transcriptional unit with aroM, a gene whose function is unknown [DeFeyter, R. C.; Pittard, J. J. *Bacteriol.*, 1986, 165, 226–232]. A 2.7 kb fragment containing the transcriptional unit had previously been isolated and cloned into pBR322 to form the plasmid pMU371 [DeFeyter, R. C.; Pittard, J. J. *Bacteriol.*, 1986, 165, 226–232]. A one kb fragment containing aroL was isolated from the plasmid pMU371 and inserted into the vector pSU19 creating the 3.3 kb aroL plasmid pKAD31 (FIG. 5). The 4.9 kb aroEaroL plasmid pKAD34 was obtained by manipulation of the flanking restriction sites of the aroE gene from pKD28 followed by its isolation and ligation into the unique XbaI and BamHI sites of pKAD31 (FIG. 6).

The aroEaroL construct D2704/pKD136/pKAD34 was able to completely remove DHS and shikimate from the culture supernatant leaving the only accumulated common pathway intermediate to be shikimate-3-phosphate. The total production of phenylalanine and phenyllactate was 3.4±0.2 mM, a slight increase from the end product production of D2704/pKD136/pKD28 but still significantly smaller than the phenylalanine and phenyllactate concentrations observed with both D2704/pKD130A and D2704/pKD136 (FIG. 3).

The aroL construct D2704/pKD136/pKAD31 was also able to completely remove DHS and shikimate from the culture broth thereby relieving the rate-limiting characteristics of both shikimate dehydrogenase and shikimate kinase with only one overproduced gene. The rate-limiting character of shikimate dehydrogenase therefore appears to be an artifact of shikimate accumulation. The importance of the removal of shikimate from the culture media on the rate-limiting characteristics of shikimate dehydrogenase suggests that shikimate may have some inhibitory effects on the enzyme. The accumulation of shikimate-3-phosphate was still observed and the total production of phenylalanine and phenyllactate was found to be 5.6±0.5 mM, the level of end product production initially observed with D2704/pKD130A and D2704/pKD136 (FIG. 3). Thus upon removing the metabolic blocks of DHQ synthase, shikimate dehydrogenase, and shikimate kinase, the total accumulation of pathway end products did not significantly increase leaving the deblocked glucose equivalents unaccounted for.

Figure 7:
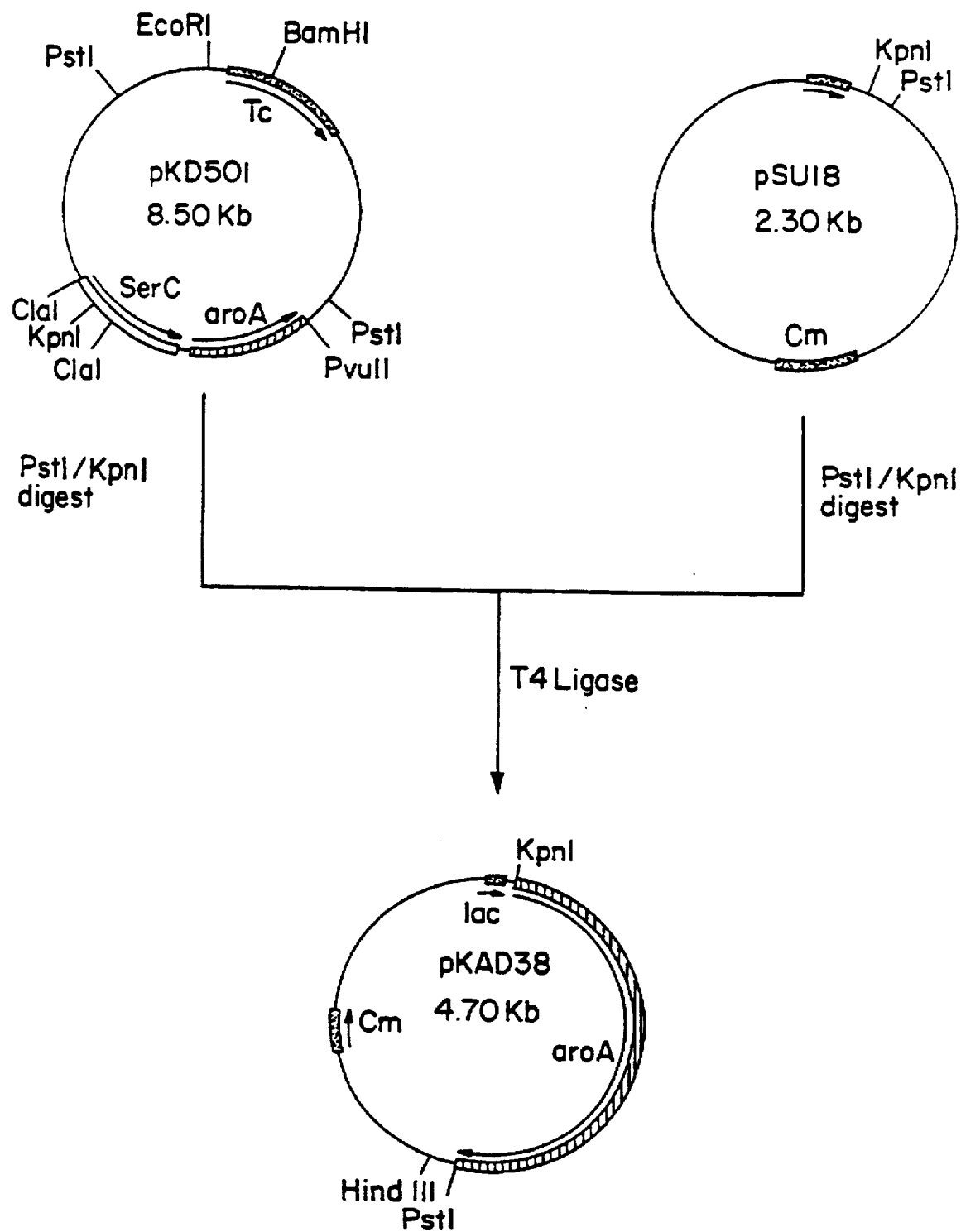
FIGS. 7–13 are similar to FIGS. 4–7 and show the construction of plasmids pKAD38, pKAD43, pKAD39, pKAD50, pKAD44, pKAD51, and pKAD42, respectively.
Figure 8:
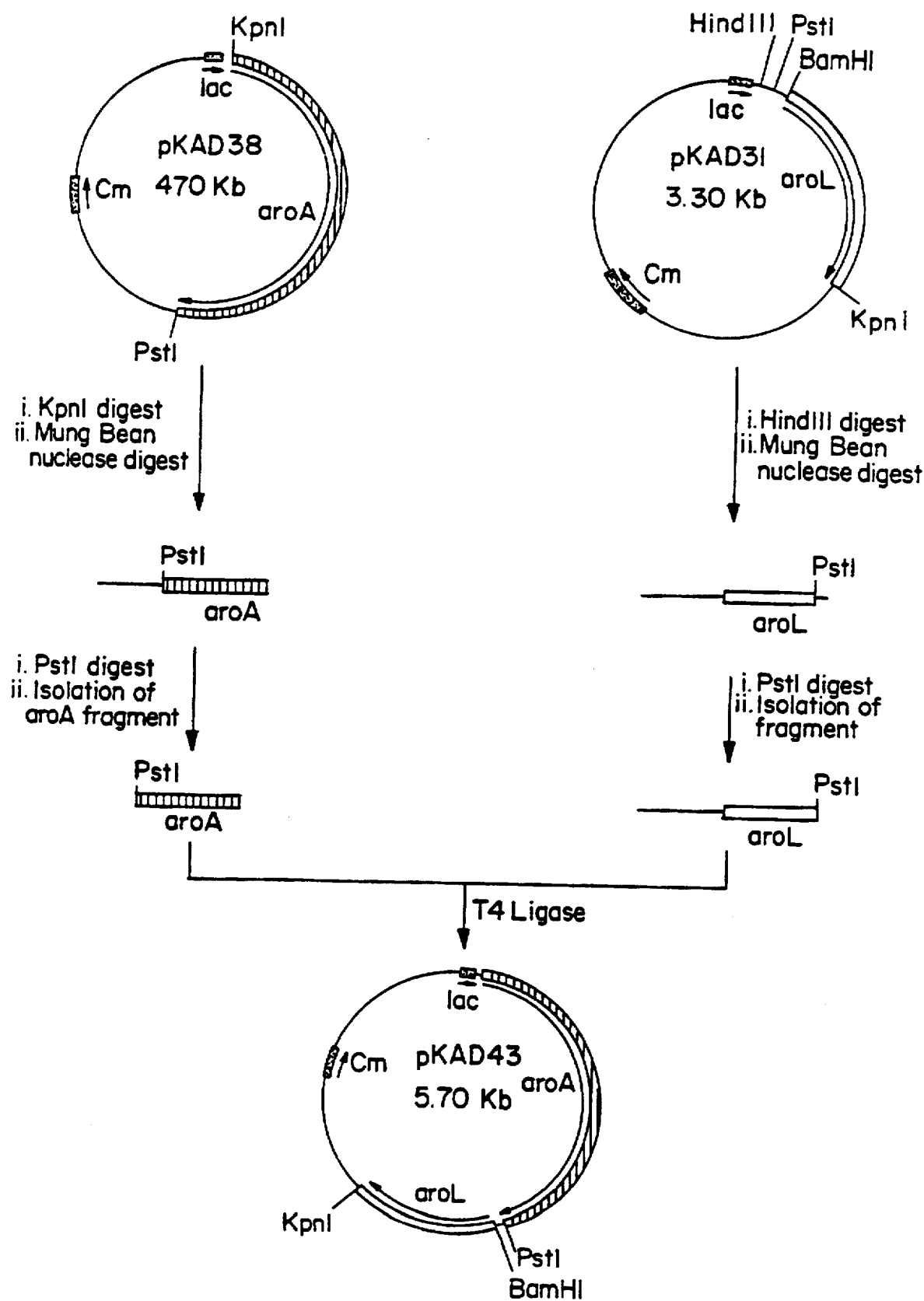

EPSP has been reported [Duncan, K.; Lewendon, A.; Coggins, J. R. *FEBS Lett.*, 1984, 165, 121–127] to be an inhibitor of the forward reaction of EPSP synthase suggesting a possible explanation for the observance of rate-limiting characteristics of the enzyme. To remove the shikimate-3-phosphate from the culture supernatant, both aroA and aroAaroL plasmids were constructed. The aroA gene exists on an operon with serC which encodes 3-phosphoserine aminotransferase, a serine biosynthetic pathway enzyme. The 4.7 kb fragment encoding the serCaroA operon has been isolated and sequenced [Duncan, K.; Coggins, J. R. *Biochem. J.*, 1986, 234, 49–57; Duncan, K.; Lewendon, A.; Coggins, J.R. *FEBS Lett.*, 1984, 170, 59–63]. To create the 4.7 kb aroA plasmid pKAD38, a 2.4 kb aroA fragment was isolated from the plasmid pKD501 [Duncan, K.; Coggins, J. R. *Biochem. J.*, 1986, 234, 49–57] and ligated into the vector pSU18 directly behind the external lac promoter (FIG. 7). Removal of aroA from the transcriptional unit of serCaroA necessitates its placement behind an external promoter for expression. A rho-independent transcription terminator that is located between the serC and aroA genes and is believed to naturally attenuate aroA expression remains intact on the 2.4 kb aroA fragment since a convenient restriction site for its removal was not available. Placement of the truncated aroA gene with the transcription terminator behind an external lac promoter should still provide some level of overexpression of EPSP synthase. The 5.7 kb aroAaroL plasmid, pKAD43 (FIG. 8), was created by isolation of the 2.4 kb aroA gene with flanking PstI and blunt ended sites and ligation into a pKAD31 vector that had been manipulated to possess equivalent sites.

Evaluation of the strain D2704/pKD136/pKAD38 revealed a significant increase in total phenylalanine and phenyllactate production producing 7.9±1.3 mM after 48 hours of accumulation (FIG. 3). Pathway intermediates accumulated in the supernatant were DHS, shikimate, and shikimate-3-phosphate. The strain D2704/pKD136/pKAD43 produced 9.7±0.3 mM of phenylalanine and phenyllactate with the accumulation of only one common pathway intermediate, shikimate-3-phosphate. The aroA plasmids gave the first indication of successful conversion of deblocked glucose equivalents to end products. The inability of the aroA gene to completely remove shikimate-3-phosphate accumulation may result from the reversibility of the reaction catalyzed by EPSP synthase.

Figure 9:
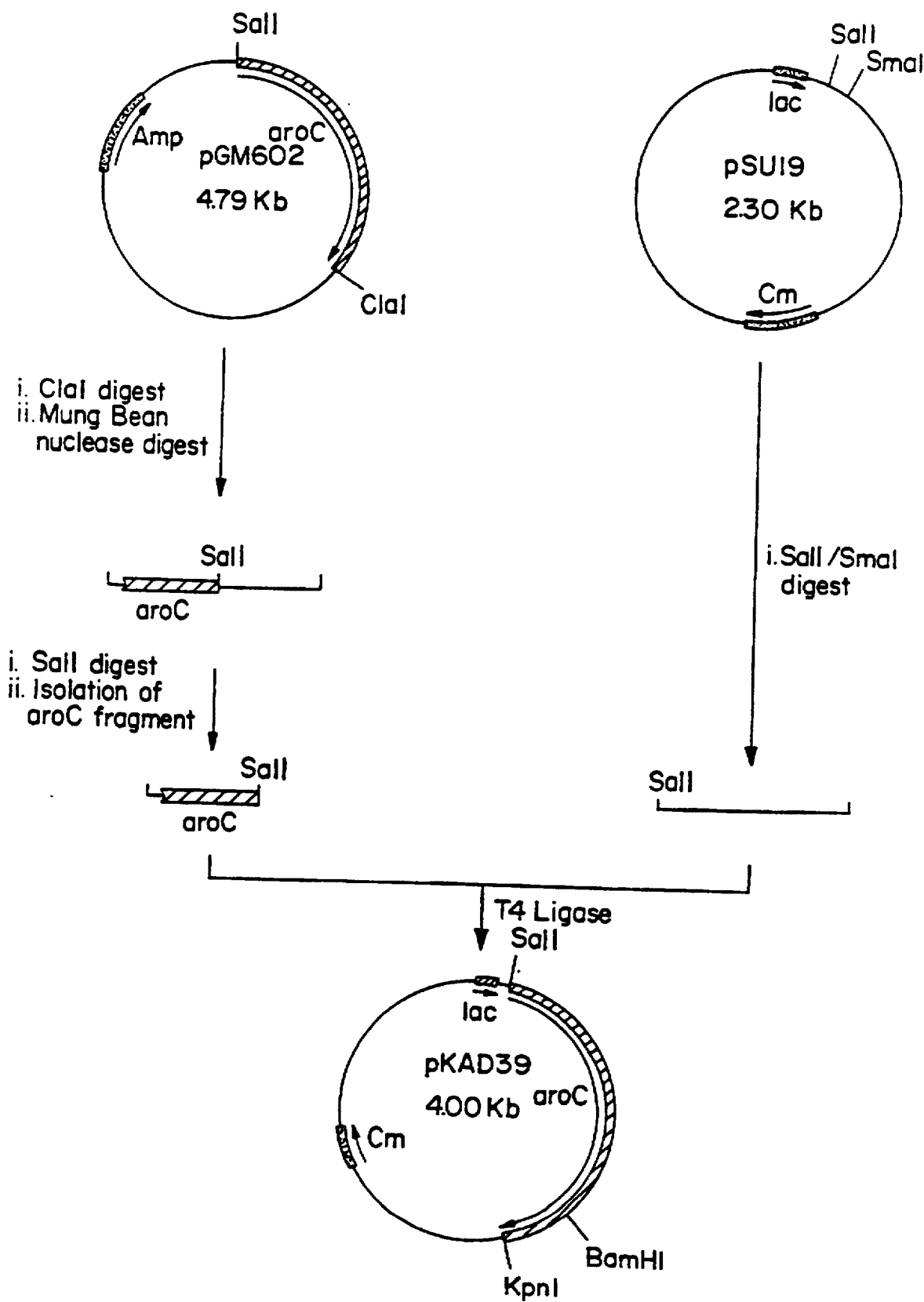
Figure 10:
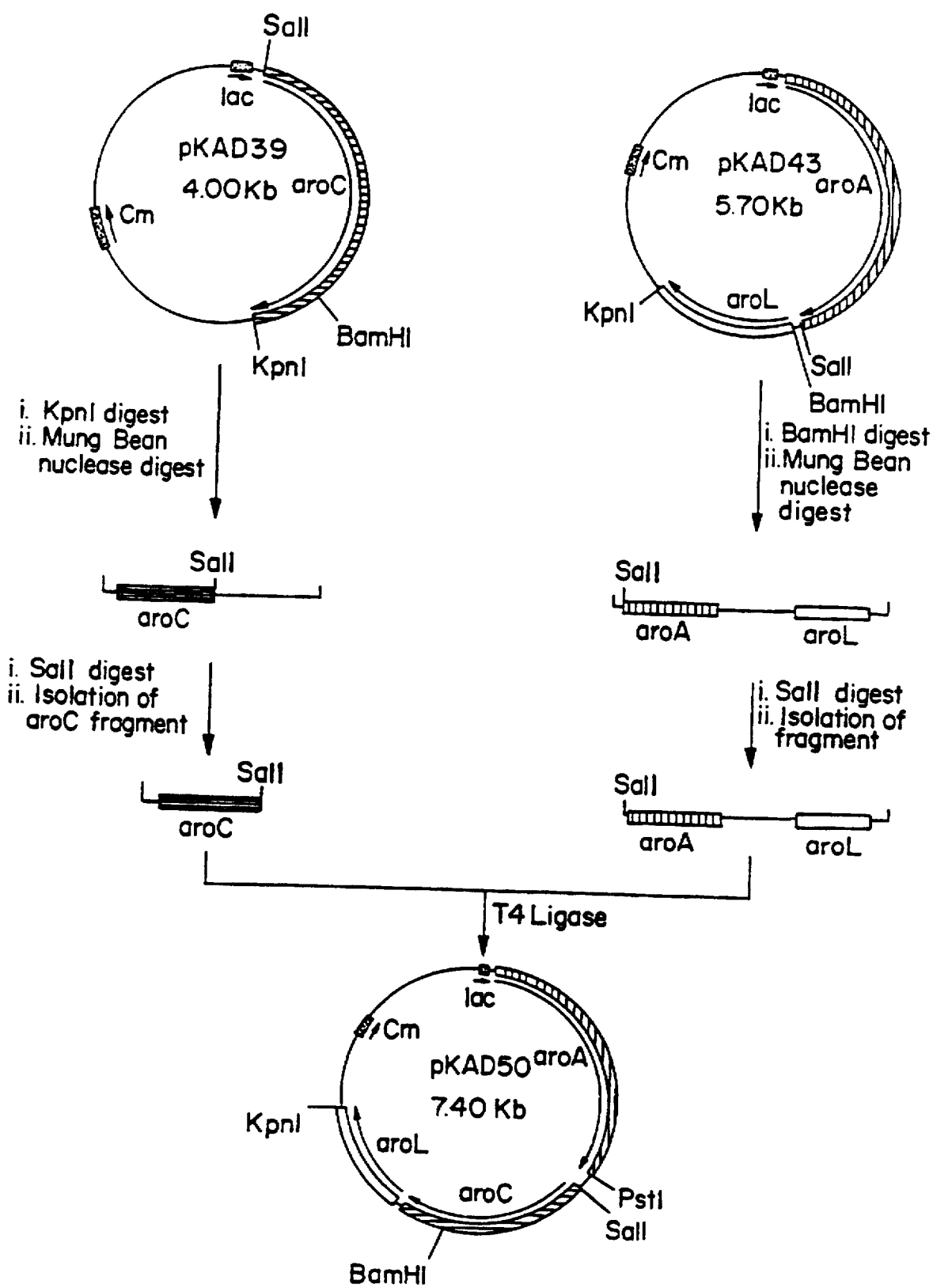

It has been suggested that chorismate synthase is both an irreversible and possibly rate-limiting enzyme [Pittard, A. J. In *Escherichia coli* and *Salmonella typhimurium*; Neidhardt, F. C., Inhgraham, J. L., Low, K. B., Magasanik, B., Schaechter, M., Umbarger, H. E., Eds.; American Society for Microbiology: Washington, DC 1987; Vol. 1, Chapter 24]. Rate-limiting characteristics of chorismate synthase might result in the continued presence of shikimate-3-phosphate if accumulations of EPSP are subsequently converted to shikimate-3-phosphate by EPSP synthase. In an attempt to completely remove shikimate-3-phosphate from the culture supernatant, an aroAaroCaroL plasmid was constructed. An aroC plasmid was first constructed by isolation of the aroC fragment flanked by SalI and blunt ended sites from pGM602 [White, P. J.; Millar, G.; Coggins, J. R.; *Biochem. J.*, 1988, 251, 313–322], a plasmid containing a 1.69 kb fragment encoding chorismate synthase. Ligation into the unique SalI and SmaI sites of pSU19 created the 4 kb plasmid pKAD39 (FIG. 9). To create the 7.4 kb aroAaroCaroL plasmid pKAD50, the 1.69 kb aroC fragment was isolated from pKAD39 as a SalI/blunt ended fragment and ligated into a pKAD43 vector that had been manipulated to contain equivalent ends (FIG. 10).

The strain D2704/pKD136/pKAD50 produced 12.3±2.2 mM of phenylalanine and phenyllactate, a significant increase in end product production over D2704/pKD136/pKAD43 (FIG. 3). While D2704/pKD136/pKAD50 still accumulated some shikimate-3-phosphate, the total amount accumulated was less than D2704/pKD136/pKAD43. The NMR of the 48 hour D2704/pKD136/pKAD50 accumulation indicates the presence of phenylalanine by resonances at δ 3.29 (dd, 14, 5 Hz, 1 H), δ 4.0 (dd, 8, 5 Hz, 1 H), and δ 7.25–7.49 (m, 5 H). Resonances for phenyllactic acid are found at δ 2.88 (dd, 14, 8 Hz, 1 H), δ 4.27 (dd, 8, 4 Hz, 1 H), and δ 7.25–7.49 (m, 5 H). A small amount of DHS is also present in the culture broth as indicated by the presence of a resonance at δ 6.4 (d, 3 Hz, 1 H). The observed increased end product production upon the addition of aroC to the deblocking plasmid has lead to the assignment of chorismate synthase as a rate-limiting enzyme with the assumption that accumulation of EPSP might be converted to shikimate-3-phosphate.

Figure 11:
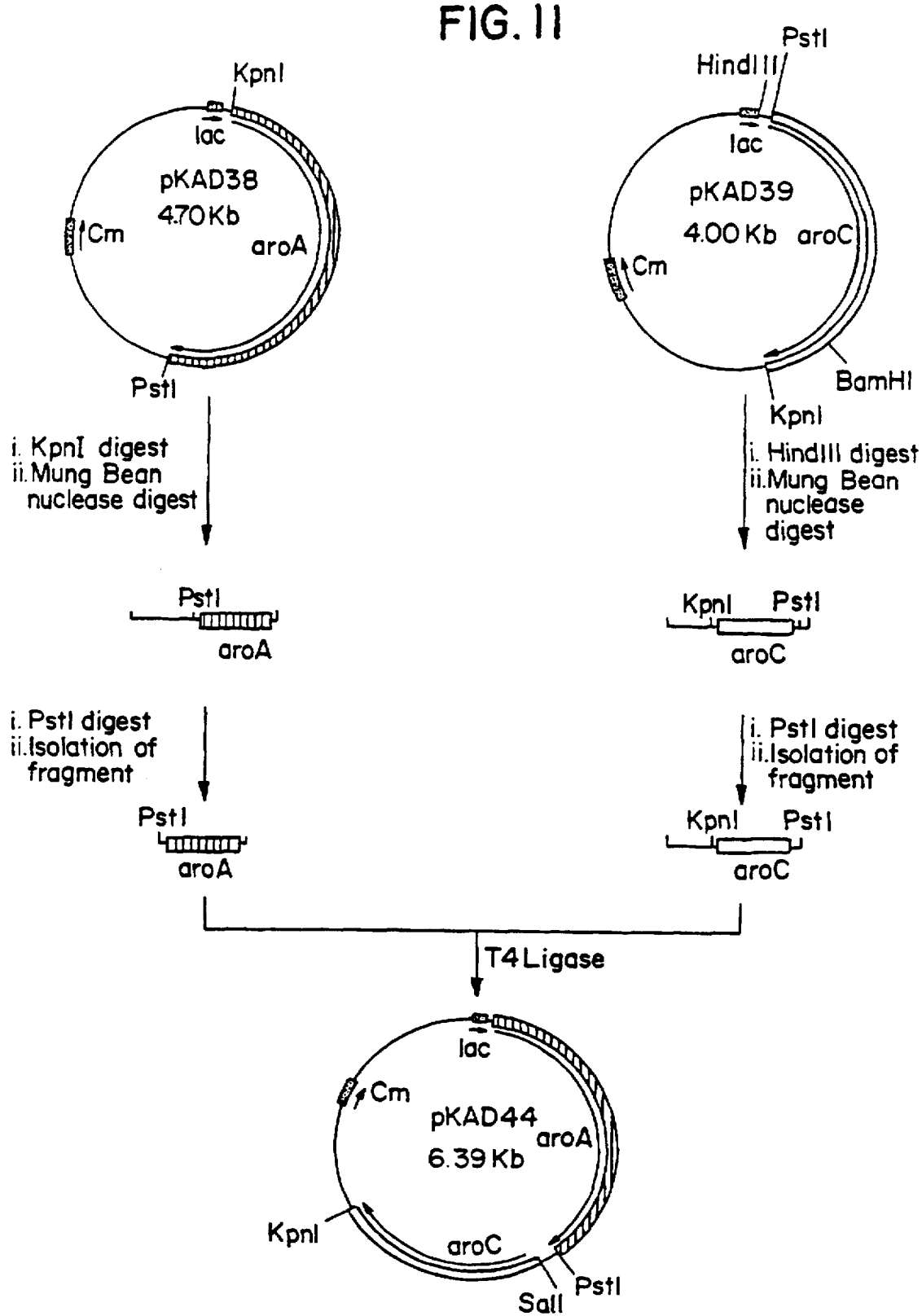
Figure 12:
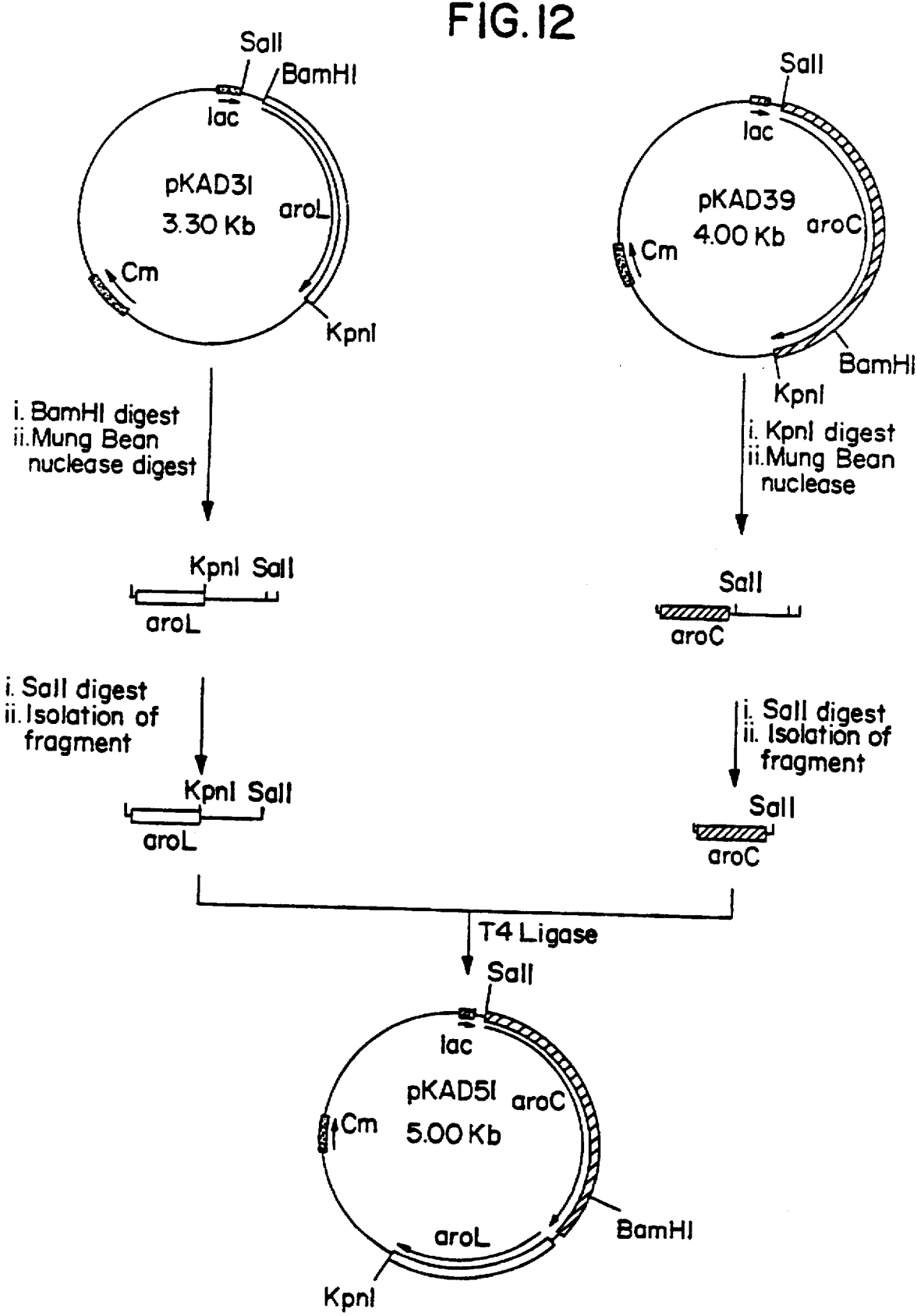

To further understand the role of chorismate synthase, plasmids containing aroC (pKAD39; FIG. 9), aroAaroC, and aroCaroL were constructed and evaluated in the strain D2704/pKD136. The 6.39 kb aroCaroA plasmid pKAD44 (FIG. 11) was created by the isolation of an aroA fragment with flanking PstI and blunt ended sites followed by ligation into a pKAD39 vector that had been manipulated to contain equivalent blunt-ended sites. The 5 kb aroCaroL plasmid pKAD51 (FIG. 12) was constructed by the isolation of aroC as a SalI blunt ended fragment which was ligated into a pKAD31 vector that had been manipulated to contain equivalent sites. As can be seen in FIG. 3, pKAD39, pKAD44, and pKAD51 did not achieve the levels of end product accumulation that the aroAaroCaroL plasmid pKAD50 achieved upon insertion into D2704/pKD136. Therefore the strain D2704/pKD136/pKAD50 was determined to be the optimum strain for maximal end product production. This bacterial cell line was deposited with the American Type Culture Collection, 12301 Parklawn Drive, Rockville Md. 20852, on Aug. 1, 1995 and assigned accession number 69876.

Figure 13:
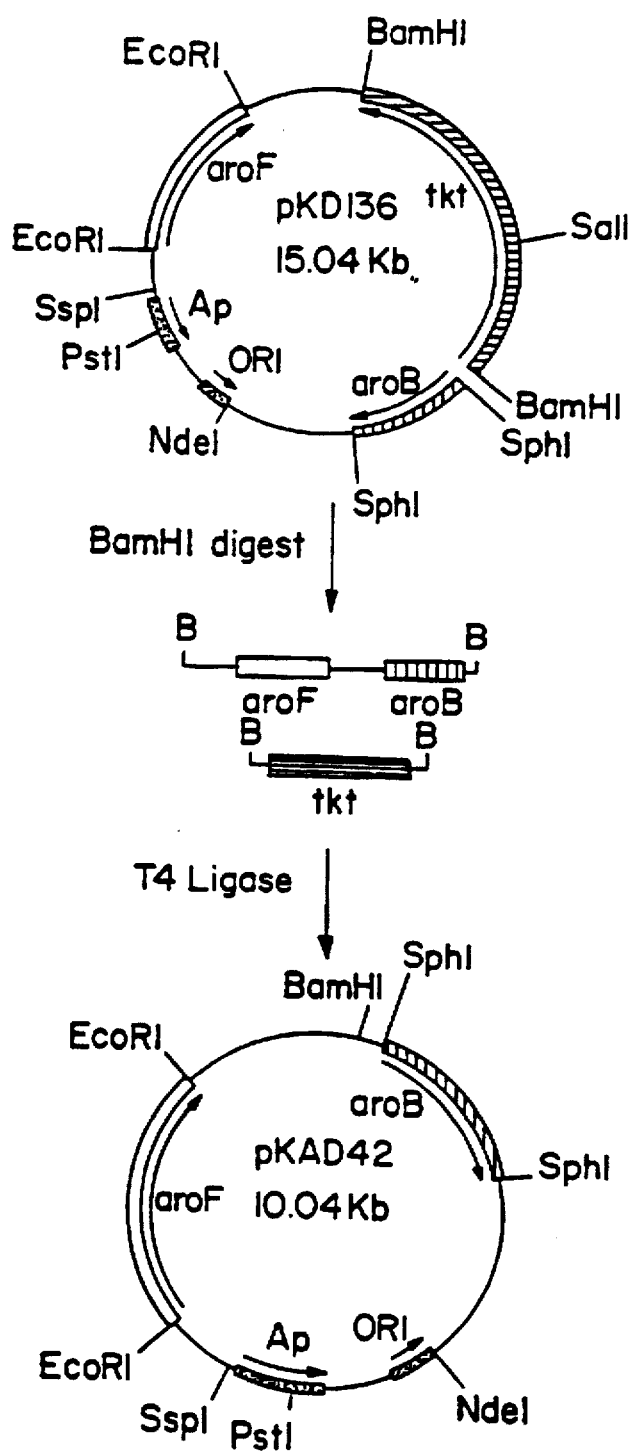

To determine the role of transketolase in the optimal strain D2704/pKD136/pKAD50, the gene was removed from the plasmid pKD136 by digestion with BamHI followed by religation creating the plasmid pKAD42 (FIG. 13). Culturing of the strain D2704/pKAD42/pKAD50 resulted in the accumulation of large amounts of acetate and lactate resulting in cell death. To alleviate this problem, the pH of the accumulation media was monitored during the 48 hour incubation and neutralized with 5N NaOH when needed. The maintenance of a neutral pH resulted in high accumulations of prephenic acid at both 24 and 48 hour time points of D2704/pKAD42/pKAD50 possibly due to the molecule's decreased ability to rearrange to phenylpyruvate at neutral pH. Thus to compare the amount of carbon flow successfully delivered to the end of the common pathway between the strains D2704/pKAD42/pKAD50 and D2704/pKD136/pKAD50, total amounts of phenylalanine, phenyllactic acid and prephenic acid were considered.

Figure 14:
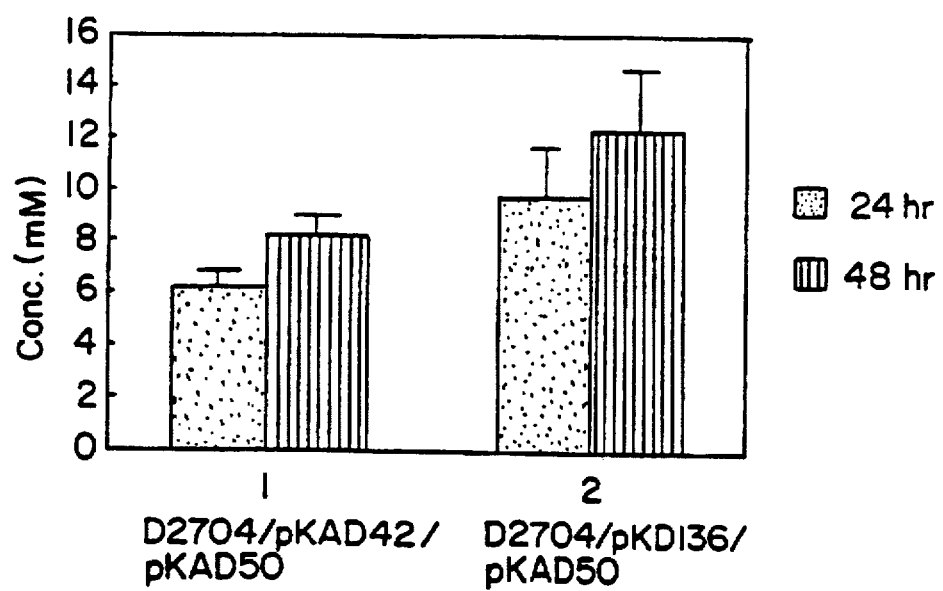
FIG. 14 is a graph illustrating the total accumulation of phenylalanine, phenyllactic acid and prephenic acid in culture medium of *E. coli* transformants of this invention.

FIG. 14 illustrates the total accumulation of phenylalanine, phenyllactic acid, and prephenic acid in *E. coli* strains D2704/pKAD42/pKAD50 and D2704/pKD136/pKAD50 after 24 and 48 hours growth in minimal media. As shown in FIG. 14, the amount of end products produced by the strain D2704/pKD136/pKAD50 was significantly larger than that produced by the strain D2704/pKAD42/pKAD50. This result shows that to successfully direct an increased surge of carbon to the aromatic amino acids and their derivatives, extra chromosomal copies of transketolase are required to increase the levels of carbon available to the common pathway as well as the genes encoding DAHP synthase, DHQ synthase, shikimate kinase, EPSP synthase, and chorismate synthase to successfully direct the surge to the desired end products.

Figure 15A:
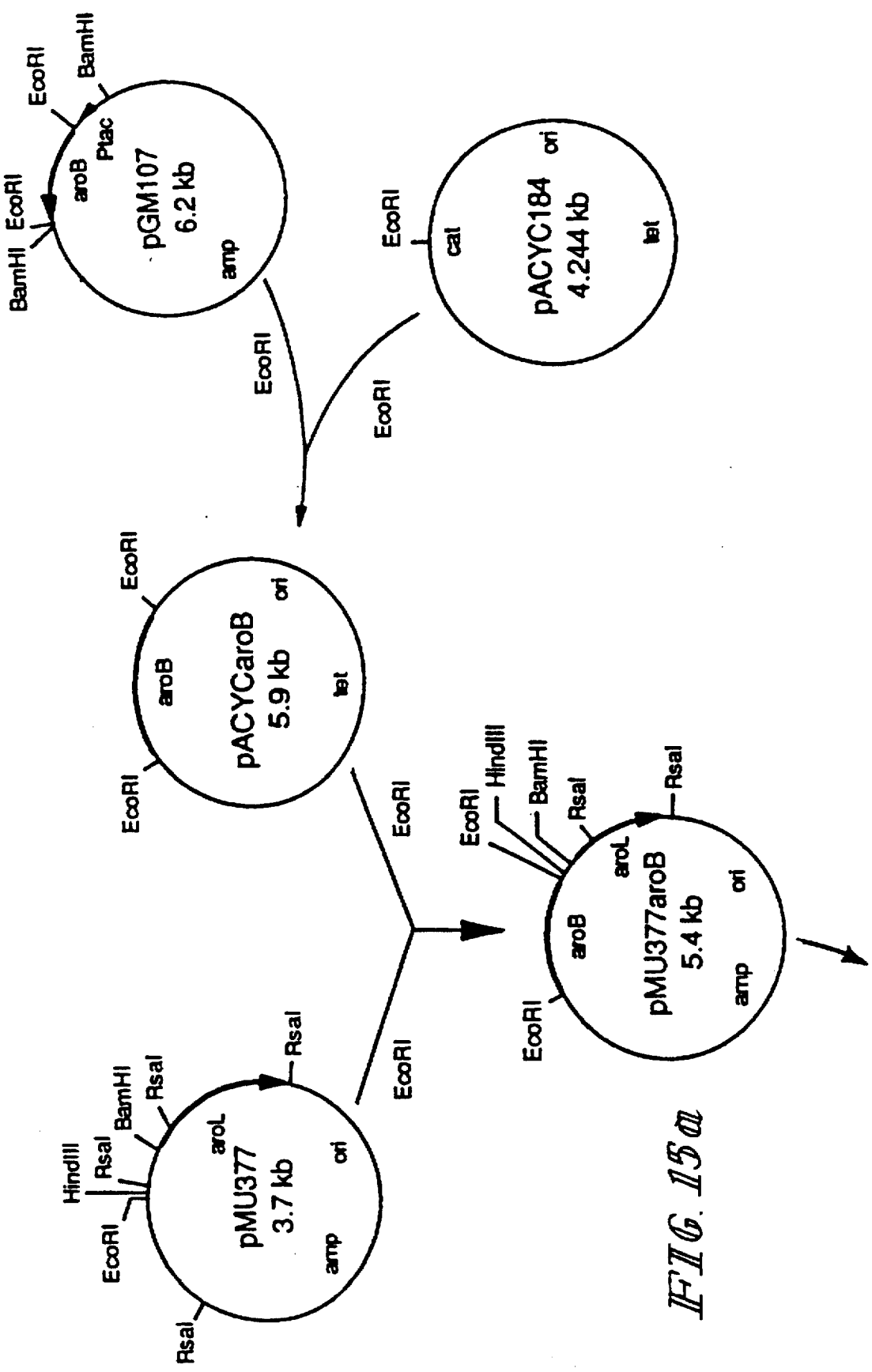
FIG. 15 illustrates the construction of plasmid pAB18B from plasmids pKAD38, pKAD39, pMU377 and pGM107.
Figure 15B:
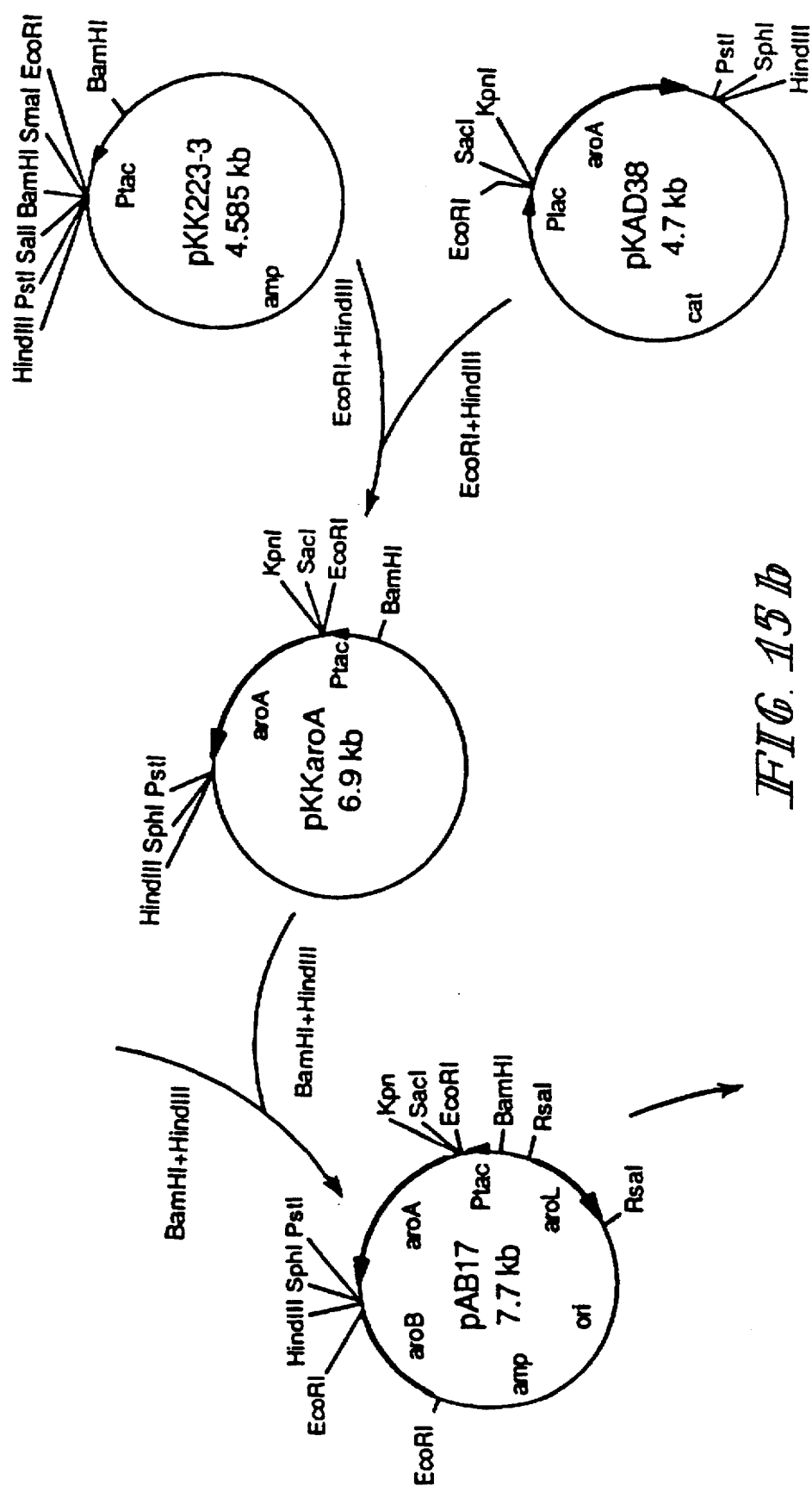
Figure 15C:
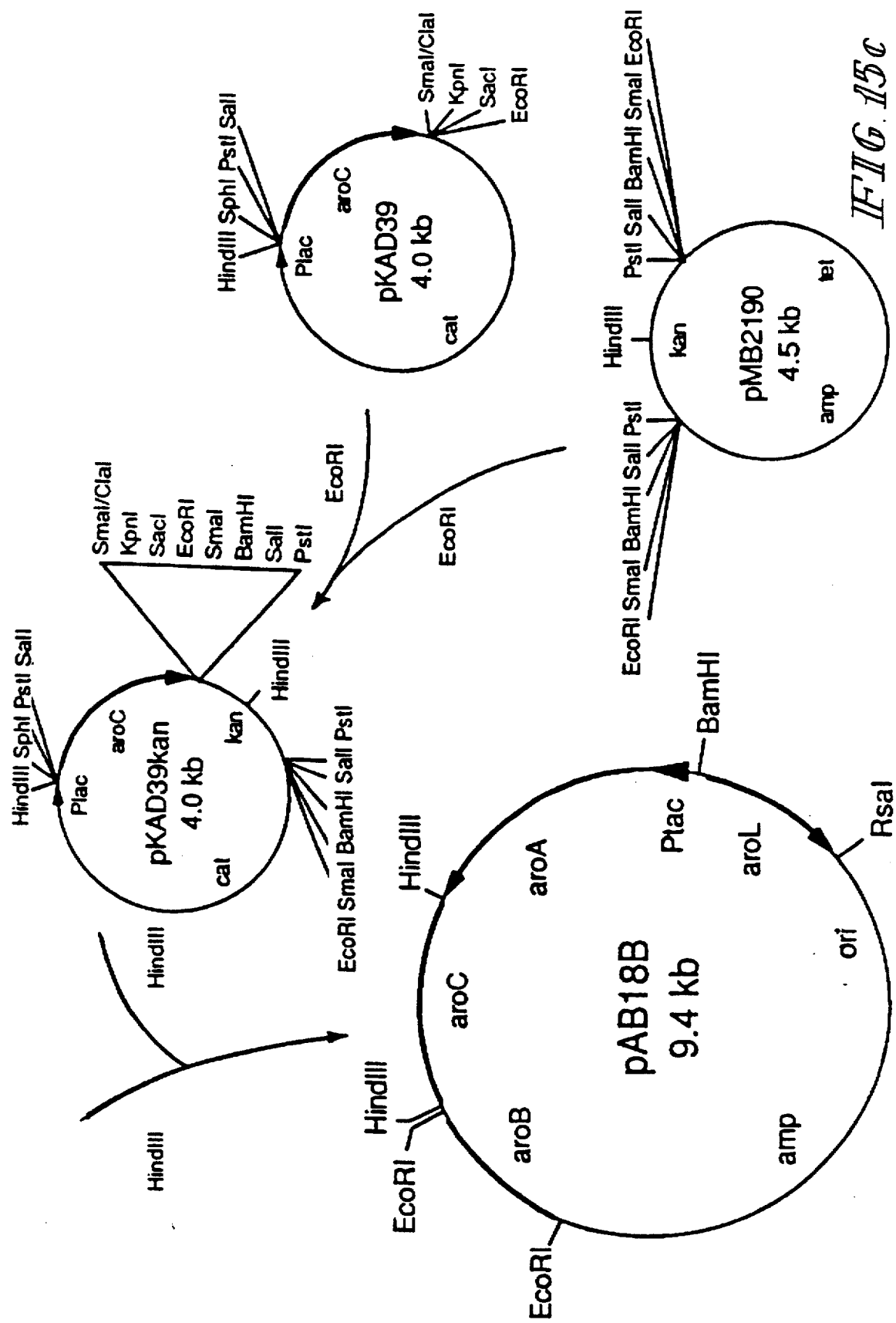

Applicants have identified DHQ synthase, shikimate kinase, EPSP synthase, and chorismate synthase as metabolic blocks in the common pathway of aromatic amino acid biosynthesis. The previous identification of shikimate dehydrogenase as a metabolic block is thought to be an artifact of shikimate accumulation in the culture media. Plasmid pAB18B was constructed from plasmids pKAD38, pKAD39, pMU377 and pGM107 and contains each of the genes that encode the rate-limiting enzymes (see FIG. 15). The construction of plasmids pKAD38 and pKAD39, providing the source of the genes aroA and aroC respectively, is described above. The construction of plasmids pMU377 and pGM107, providing the source of the genes aroL and aroB respectively, is described in references DeFeyter and Pittard, *Journal of Bacteriology*, 1986, 165, 226–232 and Millar and Coggins, *FEBS Lett.*, 1986, 200, 11–17 respectively, the disclosures of which are expressly incorporated herein by reference.

Both the yield and purity of the aromatic amino acids and their derivatives produced by biocatalytic processes can be increased by the use of plasmid pAB18B or by the employment of a two plasmid system in *E. coli*. In the two plasmid system, plasmid pKD136 or a functional equivalent is essential to committing an increased flow of carbon to the common pathway of aromatic amino acid biosynthesis while the plasmid pKAD50 or its functional equivalent is essential to successfully direct the surge of carbon to the end of the common pathway. The increased purity of the end products observed upon introduction of the deblocking genes aroB, aroL, aroA and aroC are readily discernible in the NMRs of D2704/pKD130A and D2704/pKD136/pKAD50. A summary of the data showing applicants successful enhancement of aromatic amino acid production by the common pathway is presented in Table 1.

Table 1. Summary of Experimental Data

E. coli strain D2704 was transformed with the following combinations of plasmids and the total accumulation of phenylalanine, phenyllactic acid and prephenic acid was measured after 48 hours growth in minimal media.

| PLASMIDS | OVEREXPRESSED GENES | ACCUMULATED PRODUCT |
|---|---|---|
| pKD130A | tkt, AroF | 5.5 ± .7 mM |
| pKD136 | tkt, aroF, aroB | 5.6 ± .7 mM |
| pKD136 + pKAD34 | tkt, aroF, aroB, aroE, aroL | 3.4 ± .2 mM |
| pKD136 + pKAD38 | tkt, aroF, aroB, aroA | 7.9 ± 1.3 |
| pKD136 + pKAD43 | tkt, aroF, aroB, aroA, aroL | 9.7 ± .3 mM |
| pKAD42 + pKAD50 | aroB, aroF, aroA, aroL, aroC | 8.1 ± .5 mM |
| pKD136 + pKAD50 | tkt, aroF, aroB, aroA, aroL, aroC | 12.3 ± 2.2 mM |

Replacement of plasmid-based expression with genomic-based strategies for increasing in vivo expression of enzymes is often desirable in biocatalytic syntheses. Reducing plasmid content in a cell diminishes the metabolic burden associated with expression of genes encoded by multicopy plasmids. Metabolic burden can translate into reduced product yields and instability of the plasmid construct. Genomic insertions also provide more space to insert new plasmid-borne genes into a cell. In one embodiment, an E. coli transformant is constructed wherein the E. coli is characterized by the enhanced expression of structural genes encoding for the enzymes 3-dehydroquinate synthase, shikimate kinase, 5-enolpyruvoyl-shikimate-3-phosphate synthase and chorismate synthase. This E. coli transformant comprises exogenous DNA sequences encoding at least one of the enzyme species. In one embodiment the exogenous DNA sequences are integrated into the genome of the cell. This cell transformant can be further transformed with exogenous DNA sequences encoding transketolase and DAHP synthase.

Many methods exist for genomic insertions of genetic sequences into E. coli. Successful insertions have been performed using circular plasmids, linear DNA fragments, and transposons as carrier vehicles.

Although plasmids are maintained in E. coli as extrachromosomal, circularized DNA, recombinational events occasionally occur such that plasmid DNA is integrated into the chromosome of the host cell. Exploitation of this rare event provides a method for simple site-specific insertion of a gene flanked by sequences homologous to the desired insertion region in the genome. Identification of cells with integrated plasmid DNA is difficult since both freely replicating and integrated plasmids express resistance to drugs encoded by plasmid markers. The use of a non-replicative plasmid allows for the exclusive selection of integrated plasmid DNA since cells will possess drug resistance only if the plasmid resides in the genome.

Plasmids whose replication can be switched on and off at will are desirable for genomic insertions. Normal cloning and preparation of the plasmid can be performed with replication in full operation whereas genomic insertions can be accomplished under conditions where the replication machinery is inactive. Plasmids possessing a temperature sensitive replicon are capable of being manipulated in this fashion. Plasmid pMAK705 contains such a temperature sensitive pSC101 replicon, a chloramphenicol acetyltransferase (cm) marker conferring resistance to chloramphenicol, and a convenient multiple cloning site. The plasmid is able to replicate normally when the host cell is grown at 30° C. but is unable to replicate when the host cell is cultured at 44° C. Thus genetic manipulation of the plasmids are carried out at 30° C. while integration of the plasmid into the genome can be selected for at 44° C.

Figure 16:
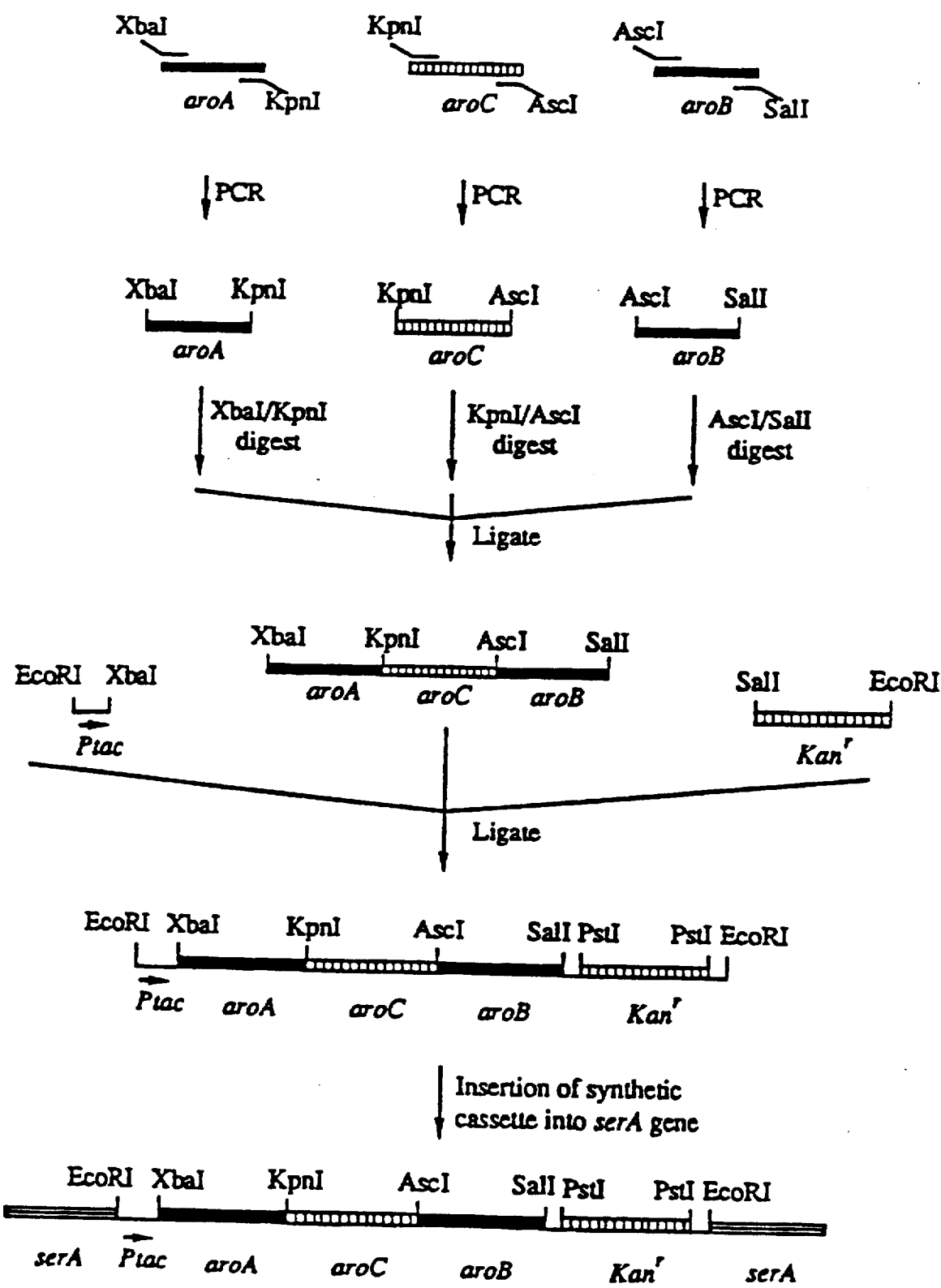
FIG. 16 illustrates the design of the synthetic cassette.
Figure 17:
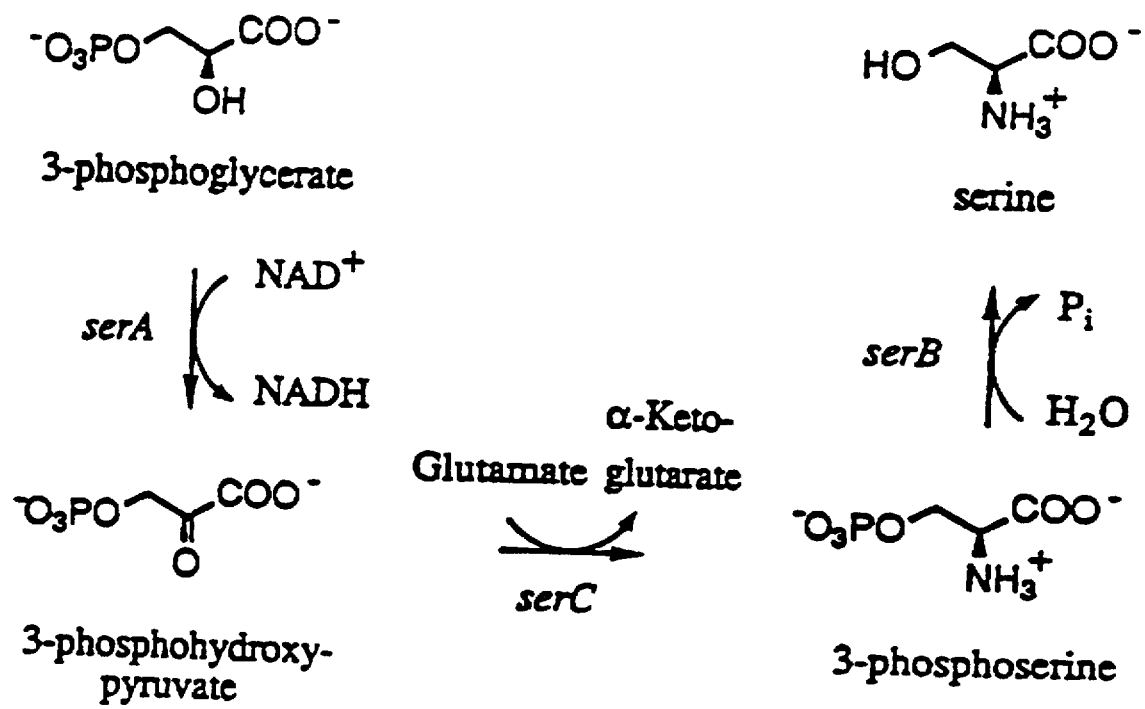
FIG. 17 illustrates the Serine biosynthetic pathway.

A synthetic cassette was designed such that the in vivo catalytic activities of the rate-limiting enzymes EPSP synthase, chorismate synthase, and DHQ synthase is amplified with a single genomic insertion of aroA, aroC, and aroB. In this set of experiments, the host cell was a tyrR– mutant which, therefore, has elevated intracellular levels of shikimate kinase. The cassette was conceived as one fragment, containing an external promoter, coding sequences for aroA, aroC, and aroB, and a fragment encoding an enzyme conferring resistance to an antibiotic (FIG. 16). The strong promoter, tac, was chosen as the external promoter to ensure sufficient transcription of aroA which lacks a native promoter. The gene encoding aminoglycoside 3'-phosphotransferase, conferring resistance to kanamycin, was chosen as the selectable drug marker for insertion of the synthetic cassette into the genome. Insertion of the cassette into the genome at serA, a locus encoding D-ephosphoglycerate dehydrogenase (FIG. 17), was planned in order to create a serine auxotroph. This auxotrophy can also be used to select for successful insertion of the synthetic cassette in the genome.

When applicants analyzed the removal of the rate limiting steps of the common pathway in the SerA auxotrophs, supplementation of serine auxotroph is not necessary since initial growth of the strain is performed in rich medium which contains serine. Subsequent resuspension of grown cells in the minimal medium used for accumulation of organic end product does not create an environment where serine is needed since the cells are simply metabolizing glucose to form phenylalanine. However, the serA locus must be present in the the serine auxotrophic cells if the auxotrophic cells are grown in minimal media, as is the case for large scale biocatalytic synthesis of medicinal and industrial chemicals. Inserting the serA locus on a plasmid and transforming a host which is serA– ensures maintenance of the plasmid provided the cells are grown in minimal medium (i.e. lacking amino acid supplementation). This approach is more economical for large scale biocatalysis than the antibiotics, and plasmidencoded resistance to these antibiotics, used to maintain the plasmids during applicants' smaller scale biocatalytic syntheses. The synthetic cassette was inserted into the genome of KAD29B (a tyrR– mutant) using homologous recombination at serA to generate cell lines KAD1D and KAD11D.

KAD1D and KAD11D were replicate plated on minimal plates with and without serine to verify that genomic insertion of the synthetic cassette disrupted the serA gene (Table 2).

Table 2. Plate Selection for Characterization of Genomic Insertion Strains

M9 plates also contained phenylalanine, tryptophan, and p-hydroxyphenylpyruvic acid to satisfy growth requirements of strains KAD29B, KAD1D, and KAD11D.

| Strain | M9/glucose | M9/glucose/ serine | LB/Cm | LB/Kan |
|---|---|---|---|---|
| JC158serA- | − | + | − | − |
| KAD29B | + | + | − | − |
| KAD1D | − | + | − | + |
| KAD11D | − | + | − | + |

Both colonies were unable to grow without supplemented serine signifying that site specific insertion into serA had occurred. Control strains JC158, a serA auxotroph, and starting strain KAD29B were replicate plated for comparison.

The in vivo catalytic activities of aroB, aroL, aroA, and aroC were measured to determine the level of expression of the rate-limiting enzymes in the strains KAD29B and KAD1D (Table 3).

Table 3. Ratios of Specific Activities of Rate-limiting Enzymes in Genomic Insertion Strains Relative to Control Strain D2704.

D2704 enzyme activity values (units mg-1) are as follows: DHQ synthase, 0.0023; shikimate kinase, 0.0023, EPSP synthase, 0.0099; chorismate synthase, 0.0017. One unit is defined as one μmol of product formed per min.

| Strain | DHQ Synthase | Shikimate Kinase | EPSP Synthase | Chorismate Synthase |
|---|---|---|---|---|
| D2704 | 1.0 | 1.0 | 1.0 | 1.0 |
| KAD29B | 1.2 | 52 | 4.1 | 1.1 |
| KAD1D | 4.8 | 7.4 | 10 | 4.9 |
| KAD1D + IPTG | 3.6 | 6.5 | 11 | 6.5 |

Insertion of the synthetic cassette into serA forming KAD1D, amplifies DHQ synthase expression by 3.6-fold, EPSP synthase by 11-fold, and chorismate synthase by 6.5-fold when IPTG is added to the media to induce the tac promoter. The high activity of shikimate kinase observed in strain KAD29B is reduced once the synthetic cassette is inserted into the genome of the strain, probably due to a metabolic burden associated with increasing the activities of the other rate-limiting enzymes.

To evaluate the effectiveness of the synthetic cassette in expressing the rate-limiting enzymes and removing the rate-limiting steps of the common pathway, applicants utilized a system that mimics genomic insertion of a plasmid through the use of a low copy plasmid. Vector pCL1920 was chosen since it contains approximately five copies per cell and has a removable lac promoter. Thus insertion of the cassette into pCL1920 without its promoter would provide a low copy vector in which the only transcription initiated would be from the tac promoter in the cassette. The synthetic cassette was removed as a 5.5 kb EcoR I fragment from pKAD72A and ligated into a 4.3 kb fragment of pCL1920, in which the promoter had been previously excised, forming the 9.8 kb low copy plasmid, pKAD77A (FIG. 18).

Figure 19A:
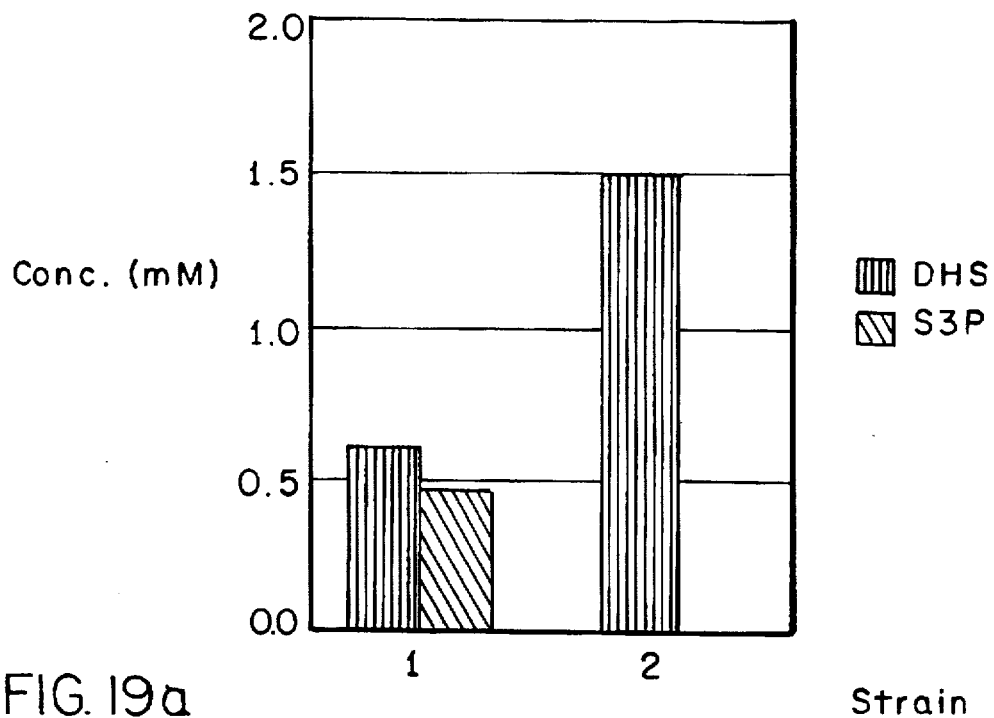
FIGS. 19 and 20 summarize common pathway end product accumulation data for several *E. coli* transformants.
Figure 19B:
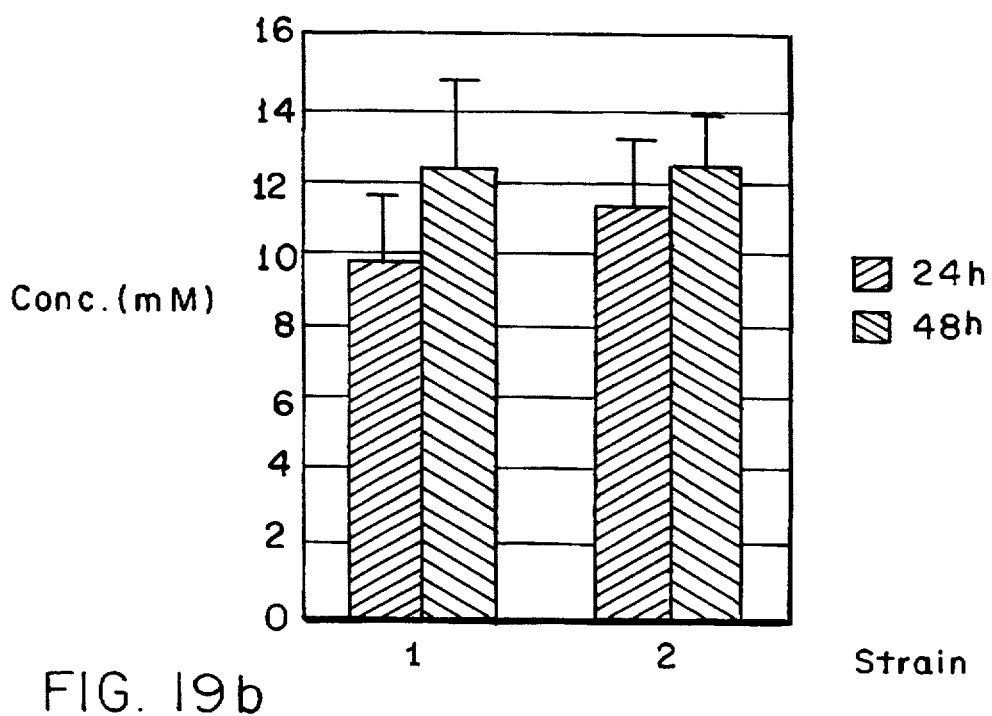

Strain KAD29B/pKD130A/pKAD77A synthesized 9.9±1.1 mM concentration of end product after 48 h of incubation. Because the pH of the culture supernatant was observed to drop to pH 5 after 24 h of culturing, cell viability was a likely problem. A second accumulation was performed where the pH was monitored during the first 24 h or incubation and neutralized when needed. Under pH controlled conditions, KAD29B/pKD130A/pKAD77A produced 12.4±1.4 mM of end products after 24 h of incubation (FIG. 19, strain 2), a value comparable to the accumulation observed with D2407/pKD136/pKAD50 (FIG. 19, strain 1). All of the glucose in the culture supernatant was metabolized during the first 24 h of minimal medium incubation and the only accumulated common pathway intermediate in the culture supernatant at 24 h was DHS (FIG. 19, strain 2).

Figure 20A:
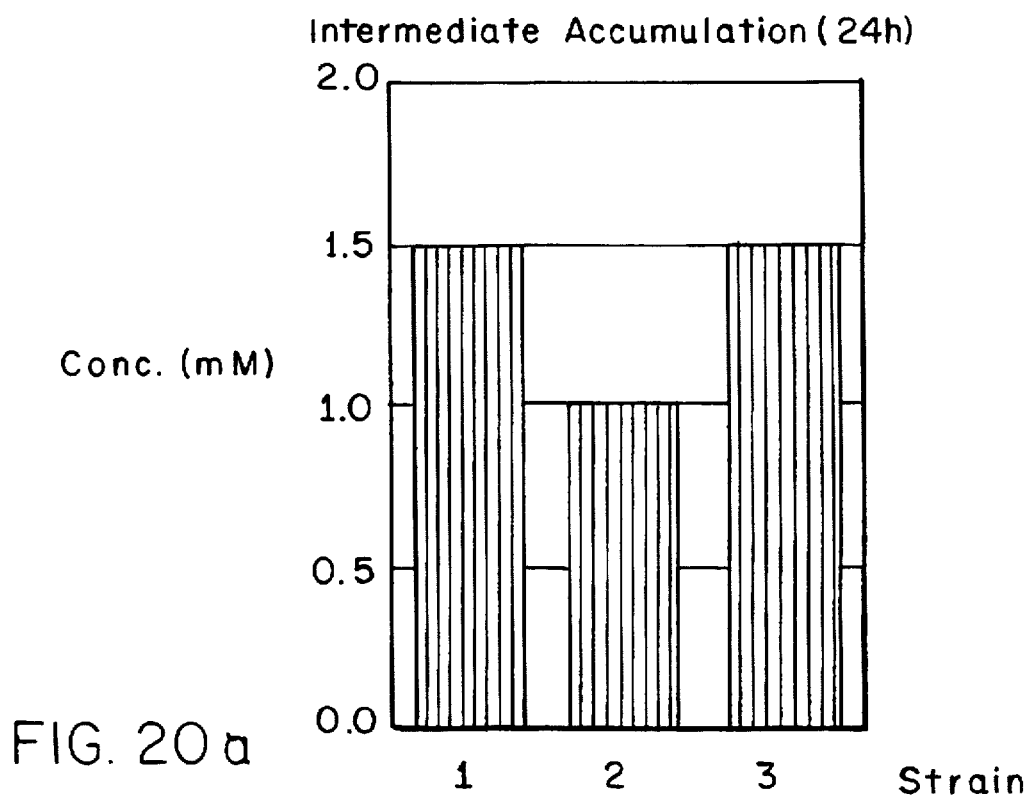
Figure 20B:
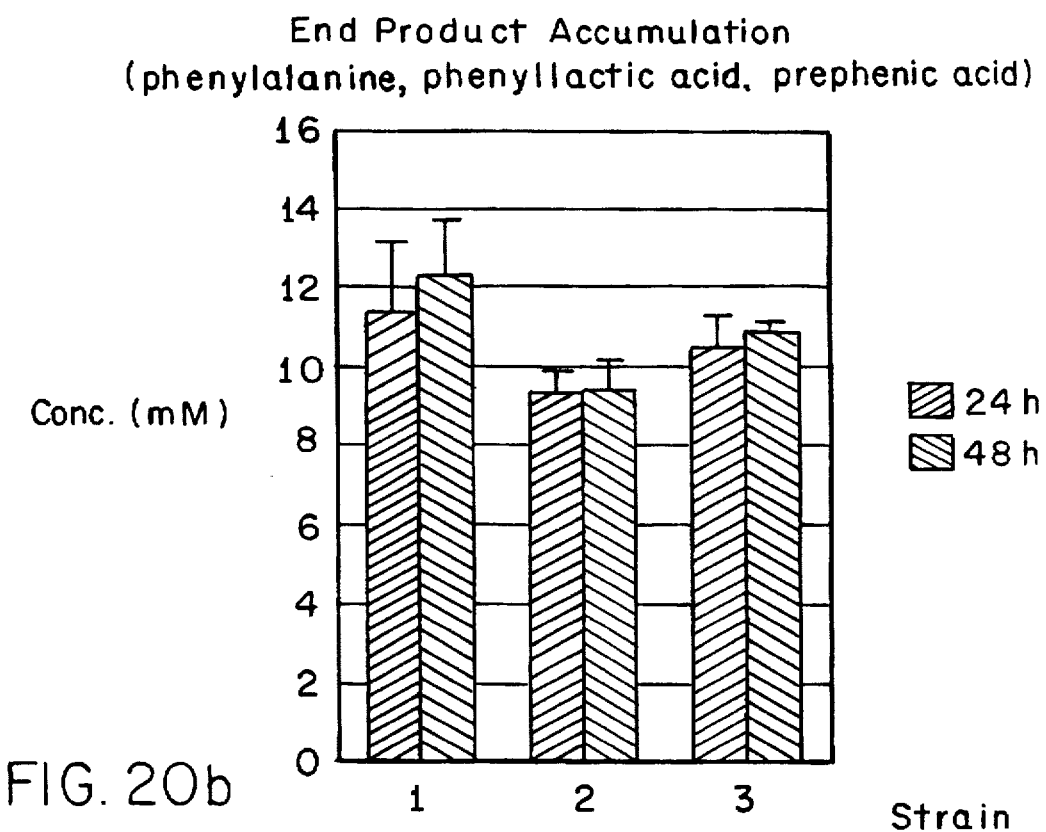

Strains KAD1D/pKD130A and KAD11D/pKD130A have exogenous sequences encoding the enzyme species 3-dehydroquinate, EPSP synthase and chorismate synthase integrated into the genome of the cell. Additional *E. coli* strains may be constructed wherein one or more of the exogenous DNA sequences encoding the enzyme species transketolase, DAHP synthase, 3-dehydroquinate synthase, EPSP synthase and chorismate synthase have been integrated into the genome of the cell. Strains KAD1D/pKD130A and KAD11D/pKD130A were constructed to test the ability of the genomic insertion to remove accumulations of substrates of rate-limiting enzymes and increase accumulations of end products. Strain KAD1D/pKD130A accumulated 9.3±0.6 mM (FIG. 20, strain 3) while KAD11D/pKD130A accumulated 10.5±0.8 mM of end products (FIG. 20, strain 3) after 24 h of incubation in minimal medium. No significant increase in end product was observed between 24 and 48 h for either strain. The only common pathway intermediate accumulating in the culture supernatants of KAD1D/pKD130A and KAD11D/pKDS130A was DHS. Both strains metabolized all of their glucose within the first 24 h of incubation and produced slightly less end product than the 12.4±1.4 mM observed in KAD29B/pKD130A/pKAD77A (FIG. 20, strain 1).

Comparison of the in vivo catalytic activities of rate-limiting enzymes for strains KAD1D and KAD1D/pKD130A revealed a significant drop in activity upon the transformation of KAD1D with pKD130A (Table 4).

Table 4. Ratios of the Specific Activities of Ratelimiting Enzymes in Genomic Insertion Strains Compared to D2704.

D2704 enzyme activity values (units mg-1) are as follows: DHQ synthase, 0.023; shikimate kinase, 0.0023; EPSP synthase, 0.0099; chorismate synthase, 0.0017. One unit is defined as one μmol of product formed per min.

| Strain | DHQ Synthase | Shikimate Kinase | EPSP Synthase | Chorismate Synthase |
|---|---|---|---|---|
| D2704 | 1.0 | 1.0 | 1.0 | 1.0 |
| KAD1D + IPTG | 3.6 | 6.5 | 11 | 6.5 |
| KAD1D/pKD130A | 1.7 | 4.1 | 2.4 | 3.1 |
| KAD29B/pKD130A/ pKAD77A | 12 | 4.0 | 12 | 25 |
| D2704/pKD136/ pKAD50 | 2.0 | 41 | 8.3 | 4.2 |

A minimum twofold drop was observed for aroB, aroA, and aroC activities. Comparison of the activities of the strains KAD29B/pKD130A/pKAD77A, containing the low copy, plasmid-based synthetic cassette, with KAD1D/pKD130A, containing the genomic insertion, revealed that KAD29B/pKD130A/pKAD77A has higher aroB, aroA and aroC activities, possibly explaining the higher accumulation values observed when culturing this strain.

EXAMPLE 1

Construction of tyrR Mutants of D2704

Introduction of the tyrR− allele into D2704 relied on phage P1 transduction. A P1 lysate was prepared from strain JB5 which is a derivative of a strain, JP2312, known to possess a mutation in the tyrR370 allele. D2704 was infected with this phage lysate and colonies possessing the tyrR mutation were selected for their ability to grow in the presence of the tyrosine analogue, m-D,L-fluorotyrosine. Because of repression of the tyrR regulon by TyrR protein in the presence of m-D,L-fluorotyrosine, colonies which are tyrR+ can not biosynthesize tyrosine thereby preventing their growth in unsupplemented medium. Growth of colonies which are tyrR– is not affected by the presence of m-D,L-fluorotyrosine since these colonies do not produce TyrR repressor protein. Transduction of tyrR into D2704 is complicated by this strain's phenotype (tyrA-, pheA-, ΔtrpE-C) which formally requires supplementation with phenylalanine, tryptophan, and tyrosine. Addition of tyrosine to the growth medium would negate the selection required for transduction of tyrR. This problem was circumvented by replacing tyrosine as a growth supplement with p-hydroxyphenylpyruvate, an intermediate directly preceding tyrosine on the tyrosine terminal pathway. Supplementation with p-hydroxyphenylpyruvate requires the D2704 variant to perform a transamination step before synthesizing tyrosine. The transaminase, encoded by tyrB, is repressed by the TyrR protein in the presence of m-D,L-fluorotyrosine. Therefore, colonies which are tyrR+ will not be able to transaminate p-hydroxyphenylpyruvate in the presence of m-D,L-fluorotyrosine. The desired tyrR– colonies will be able to grow since the absence of TyrR protein will preclude repression of tyrB transcription.

Colonies with the ability to grow on m-D,L-fluorotyrosine were replicate plated on plates with and without the analog in order to verify the initial selection for strains possessing the tyrR mutation. Growth in the absence of tryptophan, tyrosine, and phenylalanine was also tested to verify the continued presence of tyrA, pheA, ΔtrpE-C mutations. Three tyrR mutants, KAD26B, KAD27C, and KAD29B, were isolated along with a strain, KAD25A, that no longer required tyrosine supplementation to grow.

Activities of tyrR mutant strains were compared to control strain D2704 (Table 5) to determine the levels of derepression upon removal of regulation.

Table 5. Shikimate Kinase Activities of tyrRStrains Relative to D2704

| Strain | Shikimate Kinase |
| --- | --- |
| D2704 (tyrR+) | 1 |
| KAD27C (tyrR–) | 39 |
| KAD29B (tyrR–) | 52 |

KAD27C and KAD29B were found to be 39-fold and 52-fold derepressed respectively when compared to D2704. KAD29B was chosen as the strain for subsequent use since it possessed the highest in vivo shikimate kinase activity of the tyrR– isolates.

EXAMPLE 2

Construction of plasmids encoding aroA, aroC, and aroB

Sequences of aroA, aroC, and aroB were analyzed by the computer program PC Gene to find restriction sites that could be used to flank the individual genes. Flanking restriction enzyme cut sites were chosen to avoid restriction enzyme digestion of the structural genes encoding aroA, aroC, and aroB. EcoR I was chosen as the site to flank the entire cassette since a naturally occurring EcoR I lies within serA. The tac promoter was positioned first in the cassette, directly in front of the aroA fragment, since it lacks a native promoter. The sequence encoding aroC was positioned second followed by aroB and the kanamycin resistance marker.

The polymerase chain reaction (PCR) was used to assemble the synthetic cassette. Primers were designed to have a 19–20 base annealing sequence with the gene to be amplified. Additional bases were attached to the 5' end of each primer to provide convenient restriction sites for construction of the synthetic cassette (Table 6).

Figure 21:
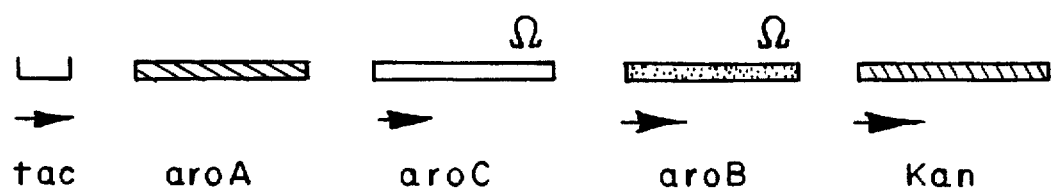
FIG. 21 illustrates the location of promoters and termination sequences in the synthetic cassette.

Primers were used to amplify the shortest possible regions that still contained promoters, ribosome binding sites, and naturally occurring transcription termination sequences at the ends of genes. Locations of native promoters and transcriptional stops included in the cassette are shown in FIG. 21.

Table 6. PCT Primers

| Gene | Primer # | Sequence |
| --- | --- | --- |
| aroA (start) | 914 (SEQ ID NO: 1) | XbaI 5'GCTCTAGAGCTATTTCTGTTGTAGAGAGTT3' |
| aroA (tail) | 915 (SEQ ID NO: 2) | KpnI 5'GTGGTACCCCATTTATTGCCCGTTGTTCAT3' |
| aroC (start) | 916 (SEQ ID NO: 3) | KpnI 5'GTGGTACCCCGAACAATATCCGGATGTTCC3' |
| aroC (tail) | 917 (SEQ ID NO: 4) | AscI 5'GGCGCGCCCCGGCACAGGTTGGGTTAT3' |
| aroB (start) | 925 (SEQ ID NO: 5) | AscI 5'GGCGCGCCACGAATCCGCTGTATGAAGA3' |
| aroB (tail) | 926 (SEQ ID NO: 6) | SalI 5'CACCGTCGACACCATTAACACCCCACTAAA3' |

Shikimate kinase activity of D2704=0.0023 units mg$^{-1}$. One unit is defined as one μmole of product formed per min.

CONSTRUCTION OF SYNTHETIC CASSETTE

Amplification of aroA

Figure 22:
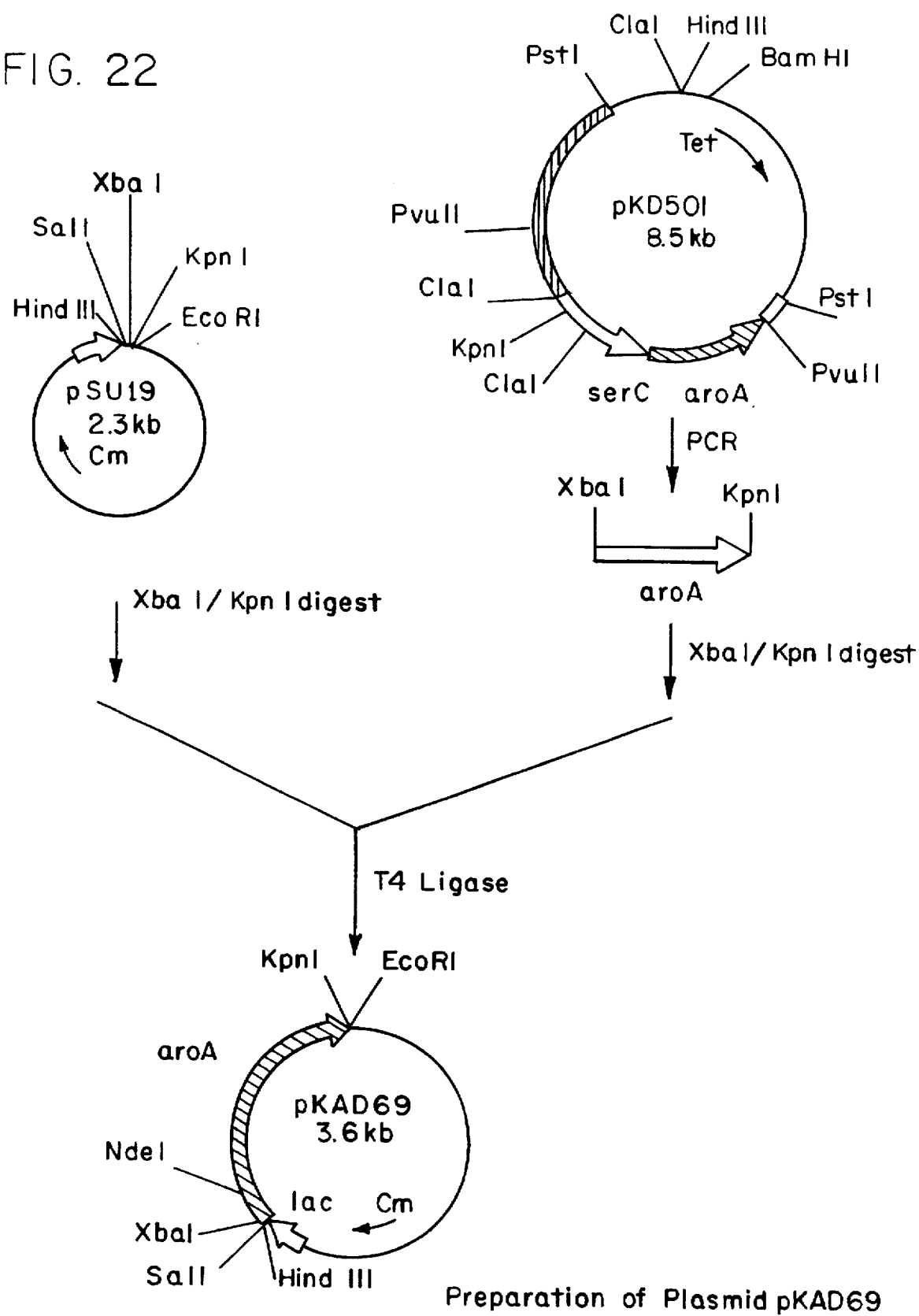
FIGS. 22–31 show the construction of plasmids pKAD69, pKAD70, pKAD68, pKAD49, pKAD62A, pKAD73, pKAD74, pKAD72A, pKAD72B, pKAD76A and pKAD80A, respectively.

Plasmid pKD501, a pAT153 derivative, was used as the source of the aroA gene. Primers 914 (SEQ ID NO:1, spanning base pairs 1465 through 1484) (Table 6) and 915 (SEQ ID NO:2, spanning base pairs 2775 through 2794) were designed to amplify a 1329 base pair fragment containing the coding sequence for aroA. Flanking regions of DNA were added to the primers to incorporate Xba I and Kpn I restriction sites at the start and tail of the gene respectively. Since it is part of an operon with serC, transcription of aroA runs off of the serC promoter located 1250 bases upstream of aroA. As a result, the amplified aroA PCR fragment did not contain a native promoter. A rho-independent termination sequence lies directly between the end of the serC coding sequence and the beginning of the aroA gene (base pairs 1440 through 1464). By using PCR, elimination of the termination sequence was possible. PCR using pKD501 as a circular template and the described primers resulted in a 1.3 kb band upon analysis by agarose gel electrophoresis. The coding sequence of aroA was isolated from the crude PCR reaction mixture by inserting the 1.3 kb aroA fragment into the Xba I/Kpn I site of vector pSU19 forming plasmid pKAD69 (FIG. 22).

Amplification of aroC

Searches upstream of the aroC coding sequence have failed to identify any exact matches of the −35 and −10 E.coli promoter consensus sequences. However, two putative sequences with limited homology have been identified. Since neither sequence has been verified experimentally, PCR primers were designed to include both sequences. Primers 916 (SEQ ID NO:3, spanning base pairs 335 through 355) (Table 6) and 917 (SEQ ID NO:4, spanning base pairs 1658 through 1676) were designed to amplify a 1341 base pair aroC fragment from plasmid pGM602, a 4.8 kb pAT153 derivative. This aroC fragment included a potential inverted repeat (base pairs 1601 through 1629) characteristic of a rho-independent termination sequence. Flanking sequences of DNA were added to the primers to incorporate Kpn I and Asc I restriction sites at the start and tail of the gene, respectively. Several attempts to amplify aroC directly from the circular pGM602 template did not give the expected 1.3 kb band upon analysis by agarose gel electrophoresis. PCR using a linear 1.7 kb aroC template, isolated from pGM602 using an EcoR I/Sal I double digest, resulted in the expected 1.3 kb band.

Figure 23:
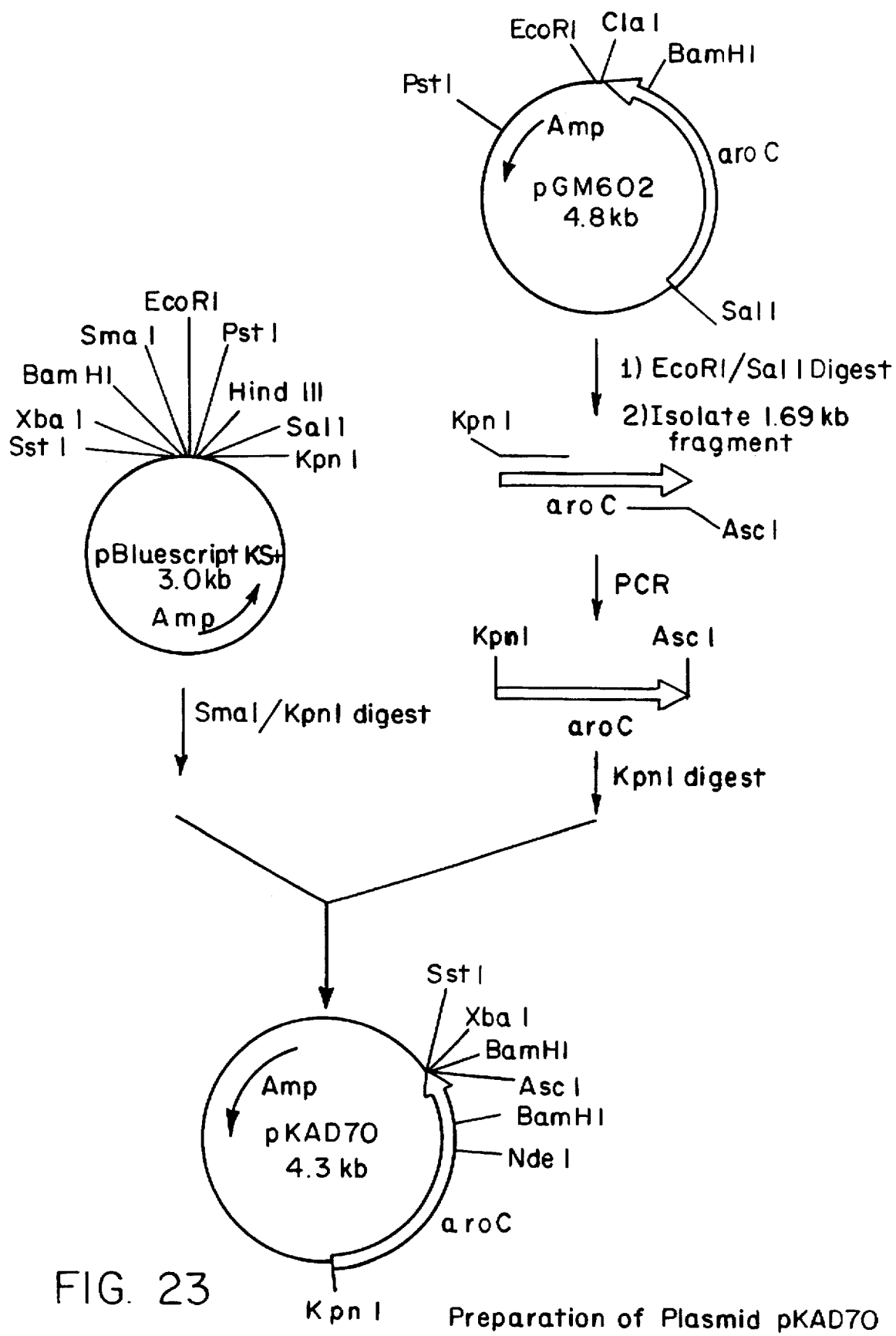

Cloning of the aroC PCR fragment is complicated by the fact that Asc I is not a restriction site in any commercially available vectors. This problem was circumvented by exploiting the blunt ends typically possessed by PCR products. Specifically, digestion of the PCR aroC product with only Kpn I yielded a fragment with a Kpn I end and one blunt end. This fragment was then ligated into the Kpn I end/blunt end of linearized vector pBluescript KS$^+$ to generate pKAD70 (FIG. 23).

Amplification of aroB

Primers 925 (SEQ ID NO:5, spanning base pairs 295 through 314) (Table 6) and 926 (spanning base pairs 1619 through 1638) were designed to amplify a 1343 base pair aroB fragment from plasmid pJB14, a 6.5 kb pKK223-3 derivative. This fragment included the native promoter and an inverted repeat downstream of the aroB gene capable of forming a stem-loop structure characteristic of a rho-independent terminator. Flanking sequences were added to the primers to incorporate Asc I and Sal I restriction sites at the start and tail of the gene, respectively. Amplification of aroB using the described PCR primers resulted in the expected 1.3 kb band upon analysis by agarose gel electrophoresis.

Figure 24:
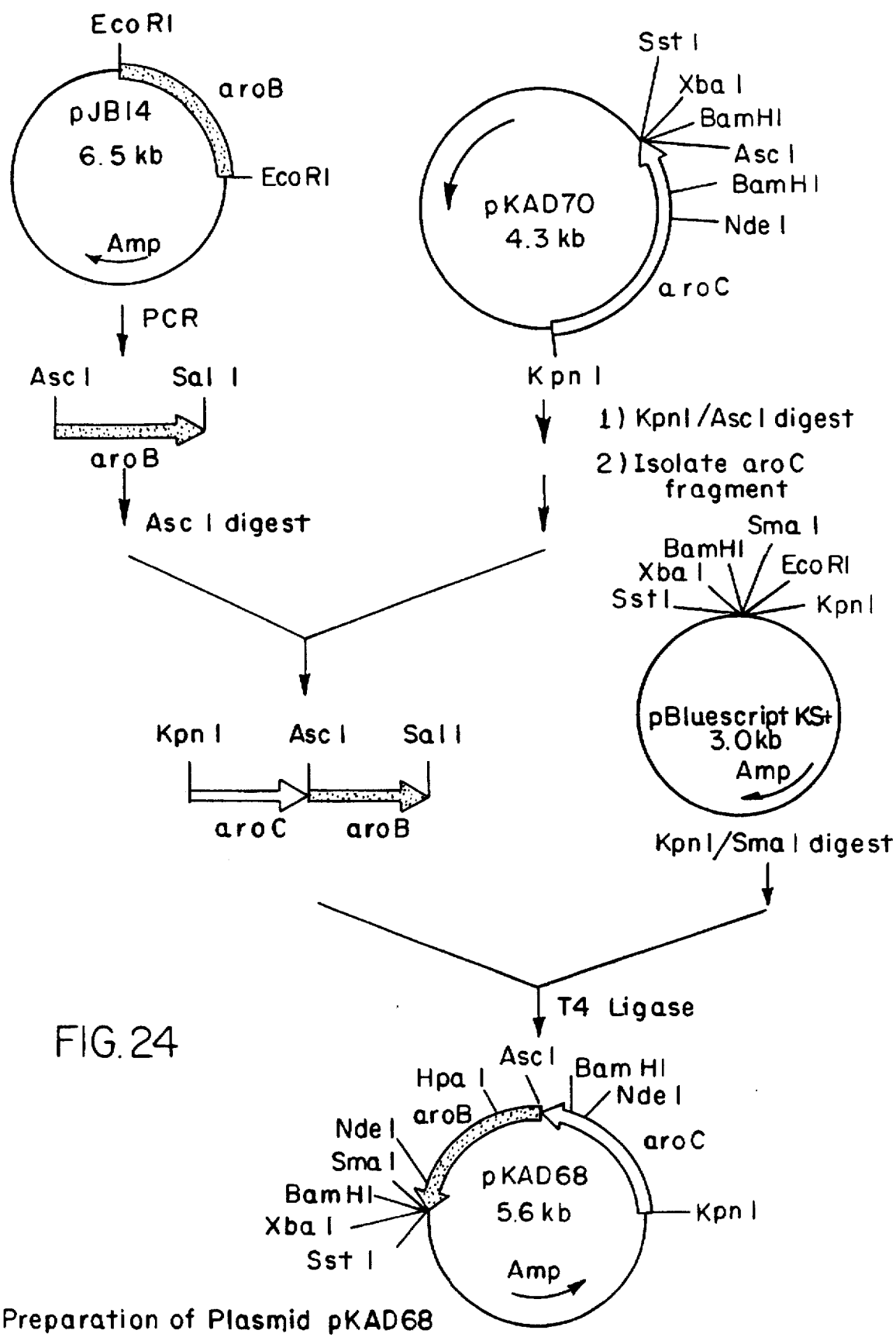

Like aroC, the cloning of the aroB fragment is complicated by the fact that Asc I is not a restriction site in any commercially available vectors. To successfully clone the aroB PCR product, the Asc I site of aroB was ligated to the Asc I site of aroC from pKAD70 (FIG. 24), forming a Kpn I/blunt end fragment. The aroC aroB fragment was cloned into the Kpn I/Sma I sites of pBluescript KS$^+$ to form pKAD68 (FIG. 24).

Plasmids containing isolated PCR products were transformed into the corresponding auxotrophic mutant strains and checked for their ability to grow on glucose without aromatic supplementation. Plasmid pKAD68, which contained the aroC aroB insert, was transformed into both AB2849aroC and AB2847aroB. Plasmid pKAD69, which carried an aroA insert, was transformed into AB2829aroA. Plasmid pKAD70, which has the aroC locus, was transformed into AB2829aroC. All plasmids successfully complemented their corresponding auxotrophic strain enabling them to grow on M9/glucose plates lacking amino acid supplementation.

While complementation of the auxotrophic mutants by the PCR plasmid isolates suggested that functional genes had been cloned, enzyme activities were measured for each host strain D2704 transformed with the respective plasmid and compared to the enzymatic activity of the host strain to verify overexpression. All plasmids were found to significantly overexpress their enzyme activities compared to the control strain D2704. Plasmids pKAD68 and pKAD70 are cloned on the high copy number pBluescript KS$^+$, a derivative of the pUC plasmids, resulting in very high overexpression of the encoded enzymes.

EXAMPLE 4

Synthesis of the Cassette

Cloning of the PCR products produced plasmids pKAD69, containing aroA, and pKAD68, containing an aroC aroB fragment. The aroA and the aroB aroC fragments were subsequently attached to fragments encoding tac and kan to assemble the full synthetic cassette.

Figure 25:
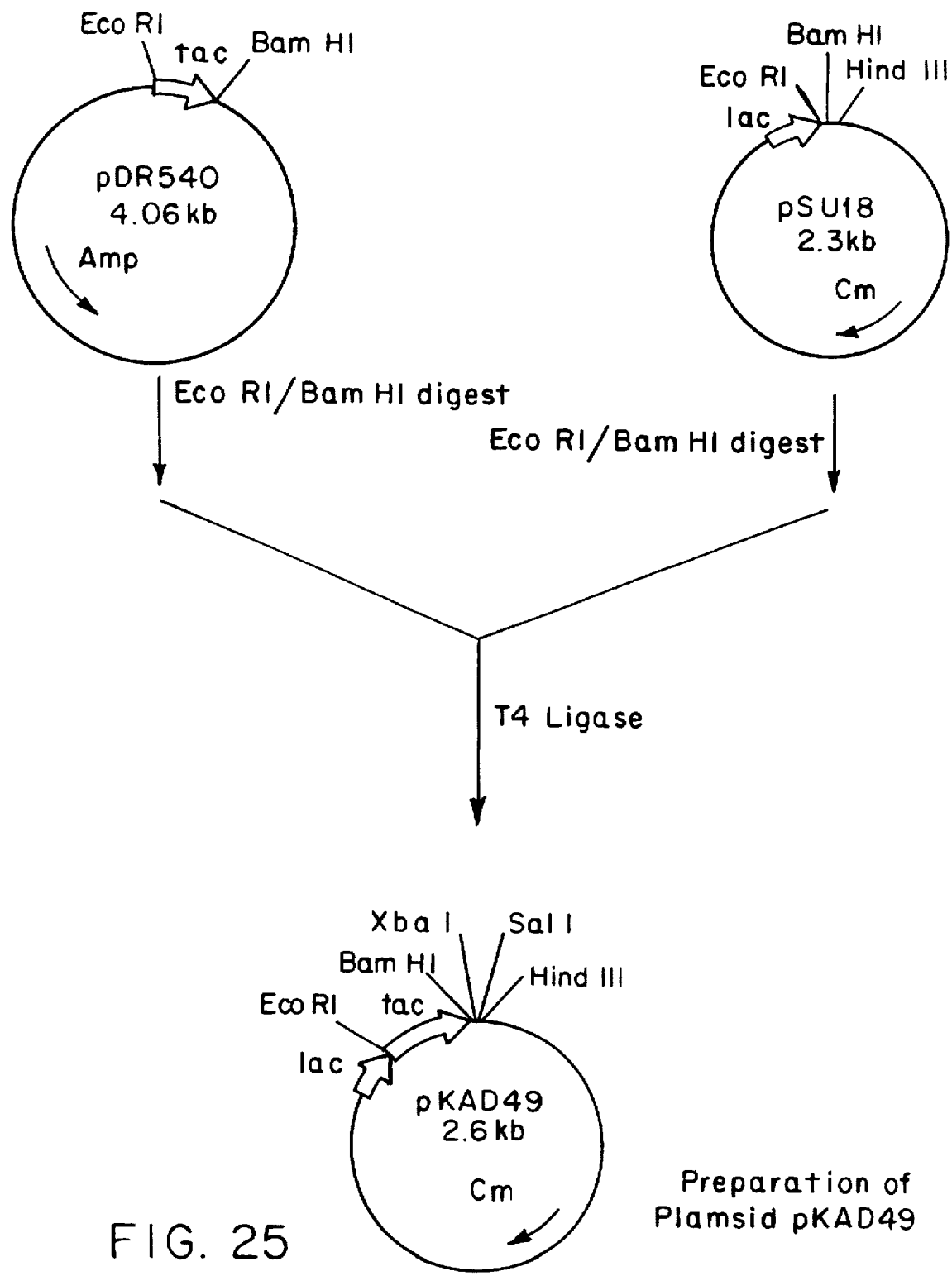

To flank the tac promoter with the necessary EcoR I and Xba I restriction sites required for its placement in the cassette, a 0.3 kb tac promoter was isolated from plasmid pDR540 as an EcoR I BamH I fragment and ligated into the EcoR I BamH I sites of pSU18 to form pKAD49 (FIG. 25).

Figure 26:
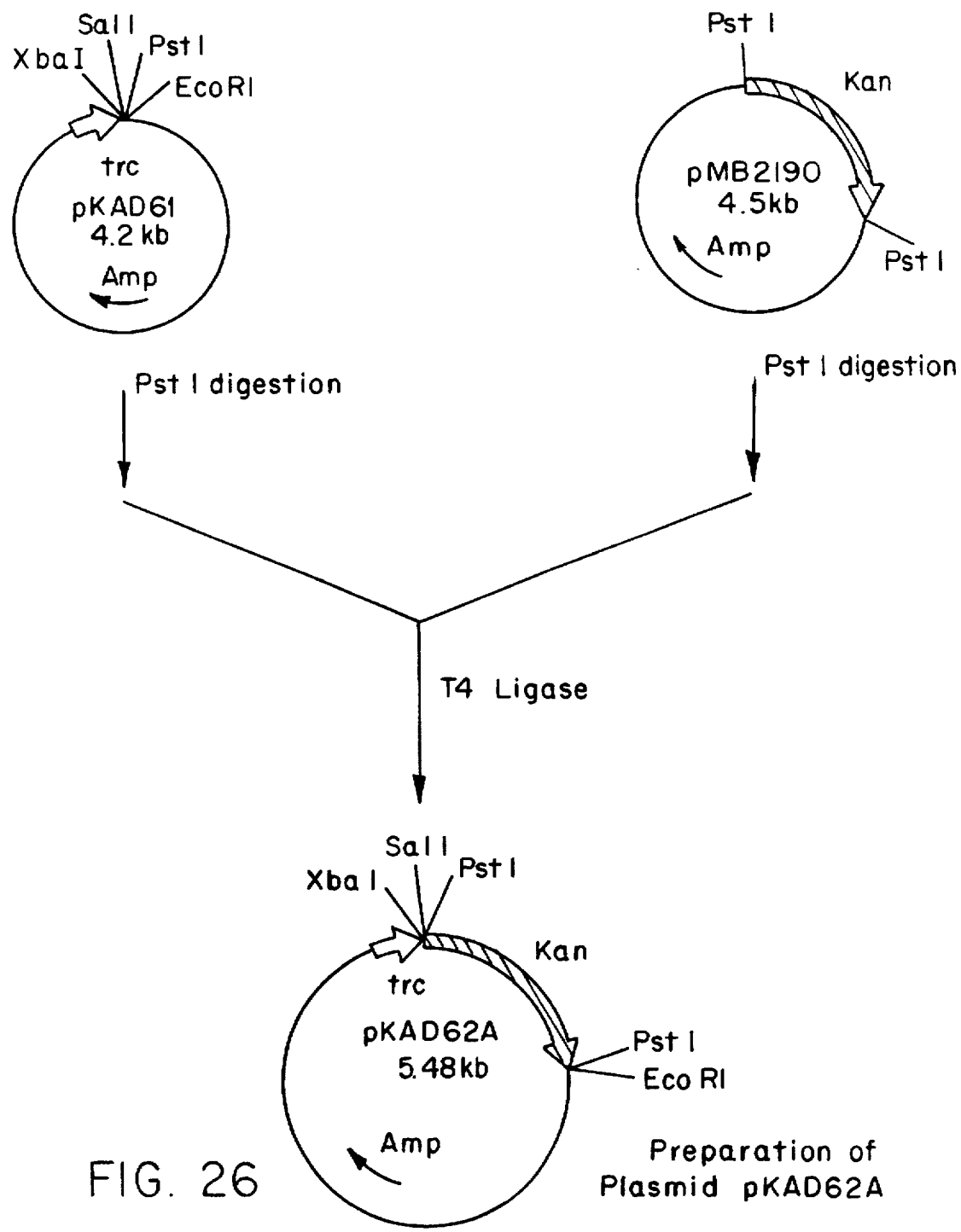

Plasmid pMB2190 was used as the source of the marker gene expressing aminoglycoside 3'-phosphotransferase (kan), conferring resistance to kanamycin. Because plasmid pMB2190 contains kan on a Pst I fragment, a number of steps were required to flank the kan locus with Sal I and EcoR I sites. Plasmid pTRC99A-E was prepared by modifying the EcoR I site of pTRC99A by EcoR I digestion, treatment of the linearized fragment with mung bean nuclease, and subsequent ligation with T4 ligase. Reinsertion of an EcoR I site into pTRC99A-E at the opposite end of the multiple cloning site was performed by digestion of the plasmid with Hind III, blunt ending with mung bean nuclease, and attachment of synthetic EcoR I linkers forming pKAD61. The kan marker gene was removed from plasmid pMB2190 as a Pst I fragment and ligated into the unique Pst I site of pKAD61 forming pKAD62A (FIG. 26). The kan fragment in pKAD62A was now flanked by the necessary Sal I and EcoR I sites for synthetic cassette construction.

A plasmid containing a tac aroA fragment was constructed by removing tac from pKAD49 as an EcoR I Xba I fragment and aroA from pKAD69 as an Xba I Kpn I fragment.

Figure 27:
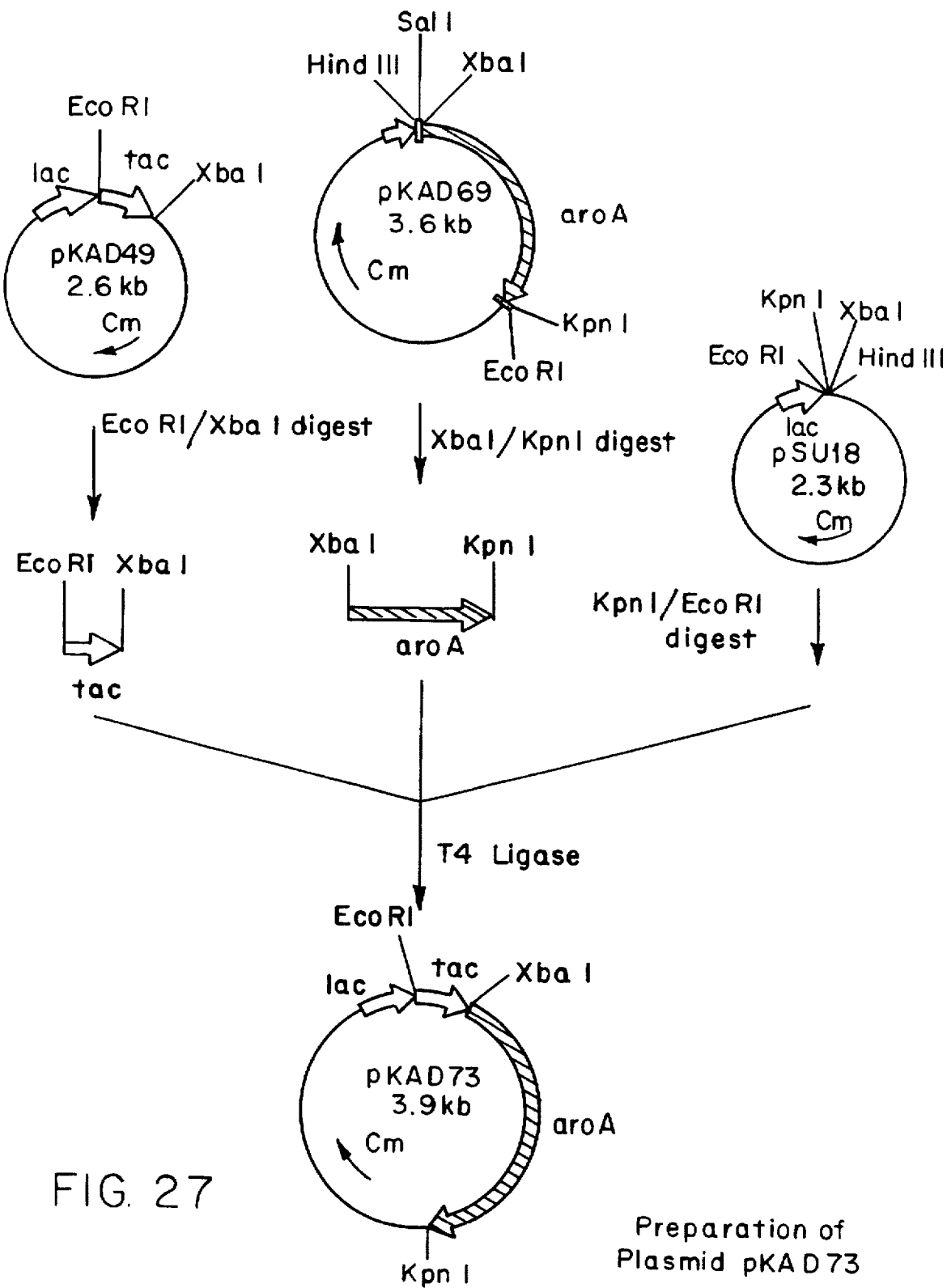

The two genes were ligated into the EcoR I Kpn I sites of pSU18 forming the 3.9 kb plasmid pKAD73 (FIG. 27).

Figure 28:
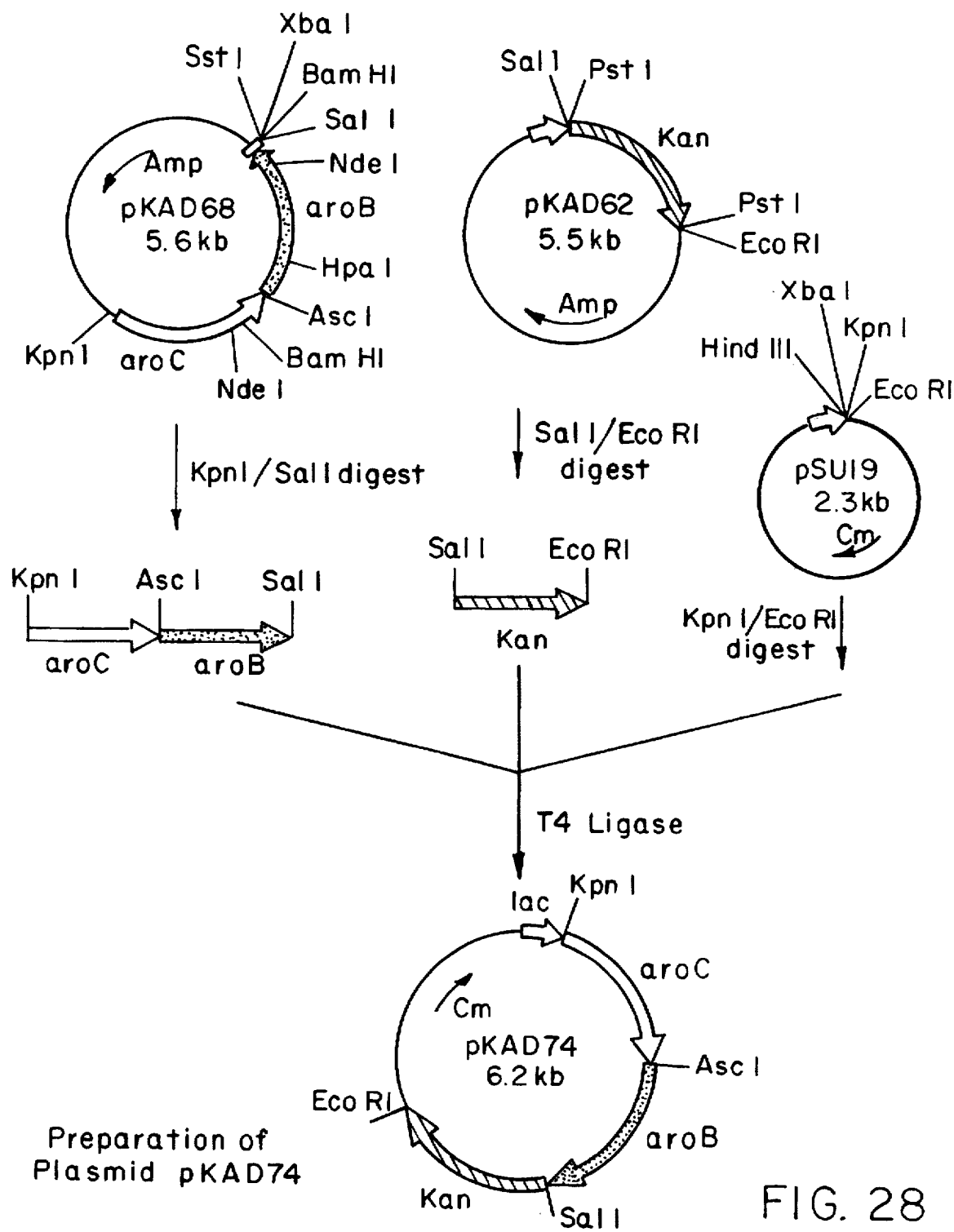

A plasmid containing an aroC aroB kan fragment was constructed by removing the aroC aroB fragment from pKAD68 as a Kpn I Sal I fragment and kan from pKAD62 as a Sal I EcoR I fragment. The two fragments were ligated into the Kpn I EcoR I sites of pSU19 forming pKAD74 (FIG. 28).

Figure 29:
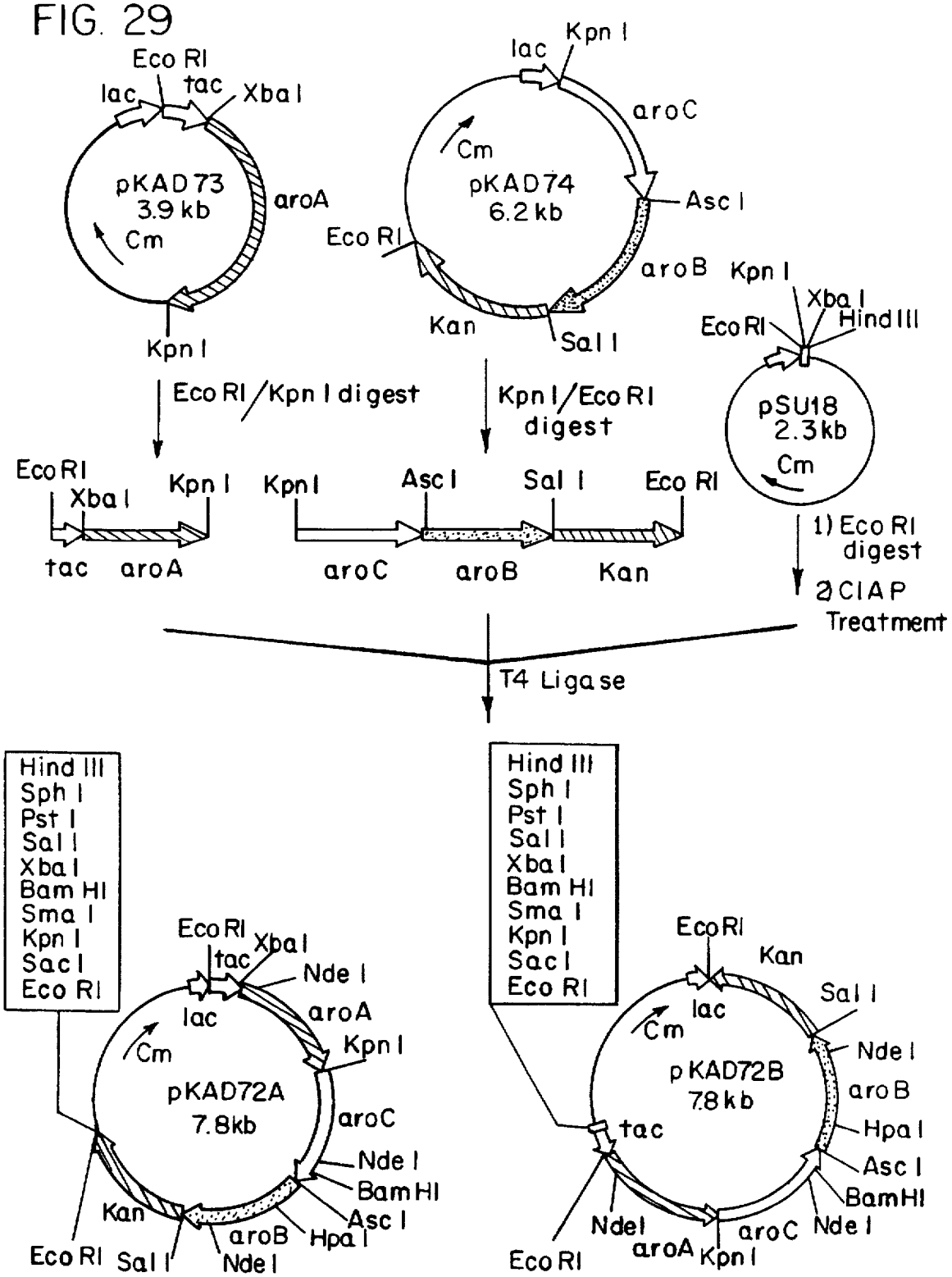

The entire cassette was pieced together by removing the tac aroA fragment from pKAD73 using an EcoR I Kpn I digest and the aroC aroB kan fragment from pKAD74 using a Kpn I EcoR I digest. Ligation of the fragments into the EcoR I site of pSU18 yielded plasmids pKAD72A and pKAD72B (FIG. 29).

EXAMPLE 5

Insertion of the Synthetic cassette into the Genome

Figure 30:
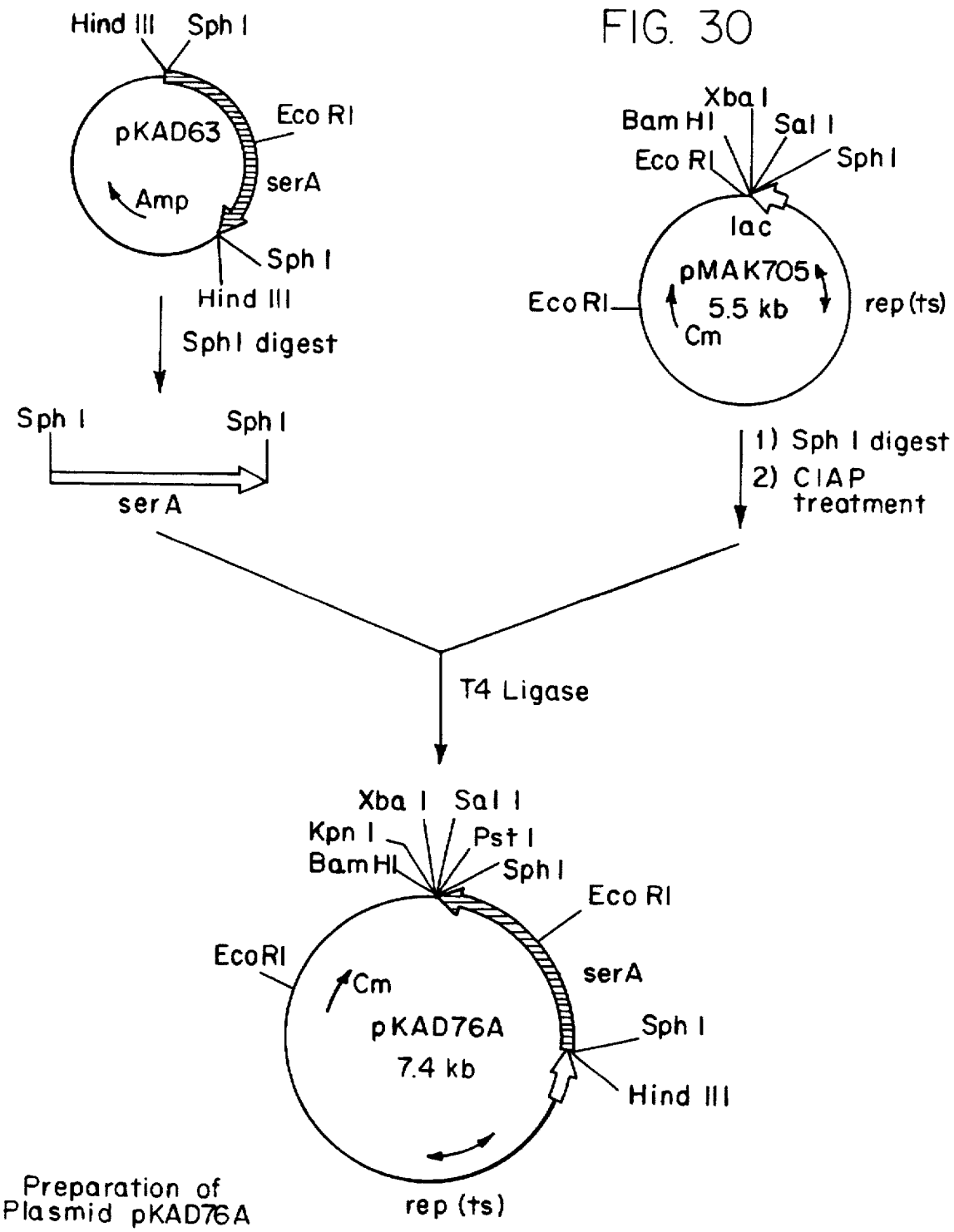

The planned insertion of the synthetic cassette into the genomic copy of serA in strain KAD29B necessitated construction of a plasmid containing the synthetic cassette flanked by serA DNA. The gene for serA was isolated from plasmid pD2625, obtained from Genencor International, as a 1.9 kb EcoR V/Dra I fragment. Both restriction enzymes result in blunt ends which allows the fragment to be introduced into the blunt end Sma I site of vector p34E[27] forming plasmid pKAD63. The serA fragment was removed from pKAD63 as a Sph I fragment and ligated into the Sph I site of the temperature sensitive plasmid pMAK705 forming pKAD76A (FIG. 30).

Figure 31:
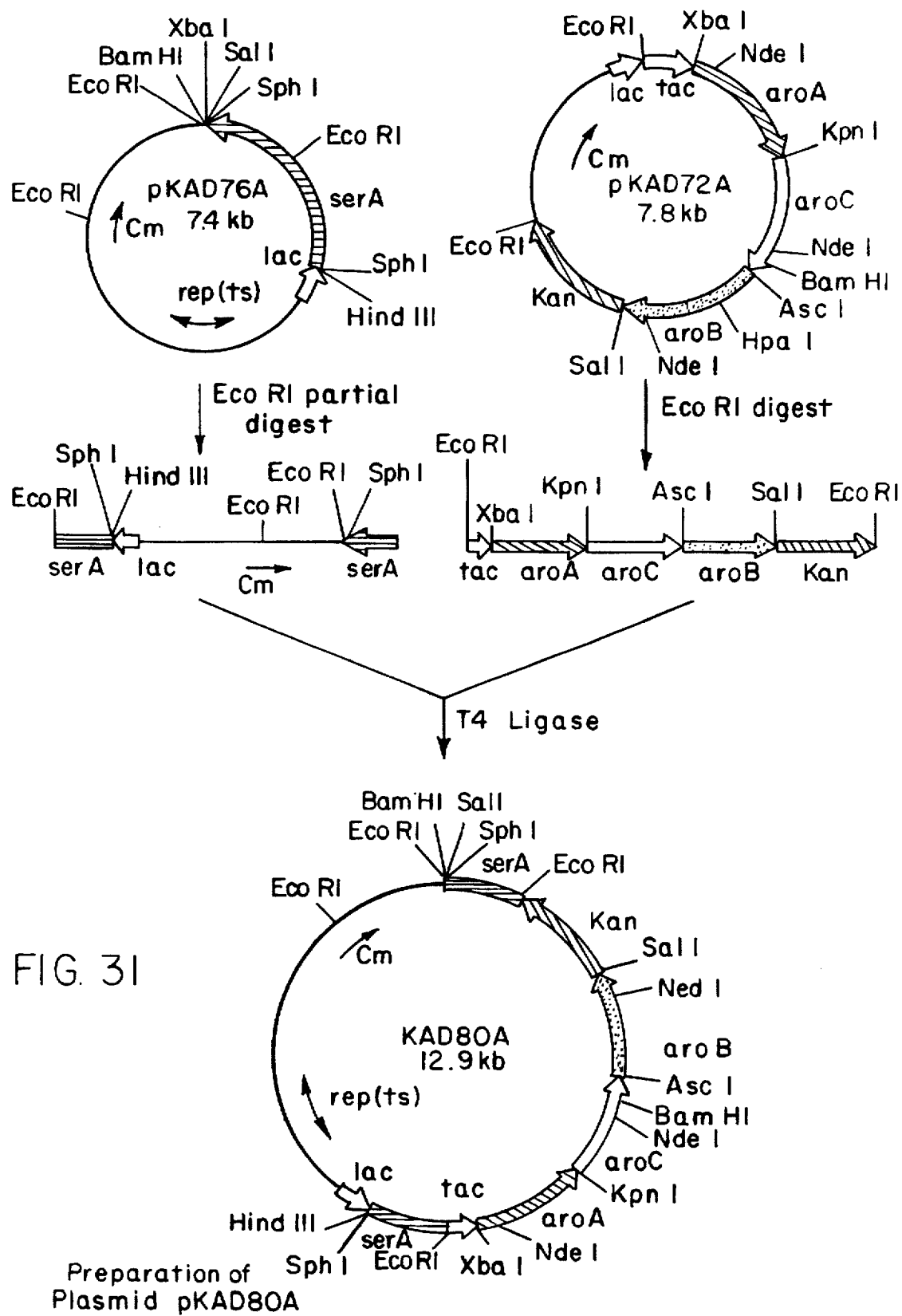

Cloning of the synthetic cassette into the EcoR I site of serA in pKAD76A was complicated by the fact that there are two other EcoR I sites in the plasmid (FIG. 31). Thus a partial digest of pKAD76A with EcoR I was performed, creating a linear 7.4 kb fragment, into which the synthetic cassette, isolated from pKAD72A as an EcoR I fragment, was ligated. The resulting 12.9 kb plasmid, pKAD80A (FIG. 31), contained the synthetic cassette flanked by portions of the serA gene in a host vector containing a temperature sensitive replicon.

The synthetic cassette was inserted into the genome of KAD29B using homologous recombination at serA. Competent KAD29B cells were transformed with pKAD80A and integration of the plasmid into the genome was selected for at 44° C. Eleven cointegrates were isolated in this manner after a series of transformations. Excision of the plasmid from the genome was performed by growing cointegrates at 30° C. in LB medium without drugs. Two more cycles of growth were carried out at 30° C. by diluting the cultures (1:20,000) into fresh LB medium without antibiotics. Growth of the cointegrate strain at a temperature permissive to plasmid replication (30° C.) creates an unstable environment for the integrated plasmid and a second recombinational event occurs allowing the excision of the plasmid from the genome. Recombination occurs such that the plasmid is either excised with its original synthetic cassette insert or with an intact serA sequence. Subsequent growth in liquid culture at 44° C. resulted in loss of the excised plasmids from the progeny.

Colonies were finally selected for kanamycin resistance and chlorampheicol sensitivity at 44° C. to identify cells that had retained the kan marker and excised the cm plasmid marker from the genome. Two such colonies were identified (KAD1D and KAD11D) and characterized further. Plasmid DNA preparations confirmed that no plasmid DNA remained in strains KAD1D and KAD11D.

To confirm that the cassette was inserted into the genome of strain KAD29B at serA, a Southern hybridization was performed. Genomic DNA was prepared from strains KAD29B, KAD1D, and KAD11D and digests of the DNA samples were electrophoresed on an agarose gel. DNA from the gel was transferred to a Nytran membrane and probed with a $^{32}$P-labeled probe of the 1.1 kb Pvu II/Kpn I fragment of serA. The resulting labeled fragments observed in the autoradigraph confirmed that site specific genomic insertion of the synthetic cassette occurred at serA in KAD1D. An extra band observed in the Kpn I/Pvu II/Asc I triple digest of KAD11D genomic DNA corresponds to incompletely digested DNA in which the synthetic cassette was inserted into serA. Since all other digest of KAD11D were correct, it was assumed that the synthetic cassette was inserted into the serA gene of KAD11D. However, due to the extra band in the KAD11D sample, analysis of genomic insertion strains focused on strain KAD1D.

We claim:

1. An *E. coli* cell characterized by the enhanced expression of a selected group of structural genes of the common pathway of aromatic amino acid biosynthesis, said selected group consisting of genes encoding the enzyme species 3-dehydroquinate synthase, shikimate kinase, 5-enolpyruvoyl-shikimate-3-phosphate synthase and chorismate synthase.

2. The *E. coli* cell of claim 1 wherein the cell comprises exogenous DNA sequences encoding at least one member of the selected group of genes.

3. The *E. coli* cell of claim 1 wherein the transformant is produced by transforming a tryR host cell.

4. The *E. coli* cell of claim 2 wherein the exogenous DNA sequences are integrated into the genome of the cell.

5. A tyrR− *E. coli* cell transformed with exogenous DNA sequences comprising gene sequences encoding common aromatic amino acid pathway enzymes wherein the DNA sequences encoding the common aromatic amino acid pathway enzymes consist of genes encoding the enzyme species 3-dehydroquinate synthase, 5-enolpyruvoyl-shikimate-3-phosphate synthase and chorismate synthase.

6. The *E. coli* cell of claim 5 wherein the exogenous DNA sequences are integrated into the genome of the cell.

7. An *E. coli* cell characterized by the enhanced expression of a selected group of genes of the common aromatic amino acid pathway enzymes, said selected group of genes consisting of genes encoding the enzymes 3-dehydroquinate synthase, shikimate kinase, 5-enolpyruvoyl-shikimate-3-phosphate synthase, chorismate synthase, transketolase, and 3-deoxy-D-arabino-heptulosonate-7-phosphate synthase.

8. The cell of claim 7 wherein the cell comprises exogenous DNA sequences encoding the enzyme species.

9. The cell of claim 7 wherein one or more of the DNA sequences encoding the enzyme species are integrated into the genome.

10. The cell of claim 8 wherein one or more recombinant plasmid vectors comprise the exogenous DNA sequences encoding said enzyme species.

11. A DNA construct comprising a selected group of structural genes encoding common aromatic amino acid pathway enzyme species, wherein the sequences of said construct encoding the common aromatic amino acid pathway enzymes consist of gene sequences encoding 3-dehydroquinate synthase, shikimate kinase, 5-enolpyruvoyl-shikimate-3-phosphate synthase and chorismate synthase.

12. A method of using a DNA construct for enhancing the production of compounds synthesized by the common aromatic amino acid biosynthesis pathway, in an *E. coli* host cell, said method comprising the steps of introducing said DNA construct into the *E. coli* host cell, said DNA construct comprising genes encoding for common aromatic amino acid pathway enzymes, wherein the DNA sequences encoding the common aromatic amino acid pathway enzymes consist of genes encoding the enzymes 3-dehydroquinate synthase, shikimate kinase, 5-enolpyruvoyl-shikimate-3-phosphate synthase, and chorismate synthase;

and culturing the cell transformant in media containing an assimilable carbon source under conditions conducive to the assimilation of said carbon source and wherein production of compounds synthesized by the common aromatic amino acid biosynthesis pathway is enhanced.

13. A plasmid construct selected from the group consisting of pKAD50 and pAB18B.

14. An *E. coli* strain selected from the group consisting of *E. coli* strain D2704/pKAD136/pKAD50, and *E. coli* strain KAD29B/pKD130A/pKAD77A.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GCTCTAGAGC TATTTCTGTT GTAGAGAGTT        30

( 2 ) INFORMATION FOR SEQ ID NO:2:

( i ) SEQUENCE CHARACTERISTICS:
        ( A ) LENGTH: 30 base pairs
        ( B ) TYPE: nucleic acid (C) STRANDEDNESS: single
            (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:2:

GTGGTACCCC ATTTATTGCC CGTTGTTCAT                                           30

(2) INFORMATION FOR SEQ ID NO:3:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:3:

GTGGTACCCC GAACAATATC CGGATGTTCC                                           30

(2) INFORMATION FOR SEQ ID NO:4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

GGCGCGCCCC GGCACAGGTT GGGTTAT                                              27

(2) INFORMATION FOR SEQ ID NO:5:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:5:

GGCGCGCCAC GAATCCGCTG TATGAAGA                                             28

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (i i) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

CACCGTCGAC ACCATTAACA CCCCACTAAA 30